(12) United States Patent
Matsumura et al.

(10) Patent No.: US 11,980,438 B2
(45) Date of Patent: May 14, 2024

(54) PHYSIOLOGICAL INFORMATION TRANSMISSION SYSTEM, PHYSIOLOGICAL INFORMATION DETECTION SENSOR, INFORMATION PROCESSING APPARATUS, AND PHYSIOLOGICAL INFORMATION TRANSMISSION METHOD

(71) Applicant: NIHON KOHDEN CORPORATION, Tokyo (JP)

(72) Inventors: Fumiyuki Matsumura, Tokyo (JP); Norihito Konno, Tokyo (JP); Minori Hosoi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 4 days.

(21) Appl. No.: 16/609,916

(22) PCT Filed: Apr. 25, 2018

(86) PCT No.: PCT/JP2018/016778
§ 371 (c)(1),
(2) Date: Oct. 31, 2019

(87) PCT Pub. No.: WO2018/203502
PCT Pub. Date: Nov. 8, 2018

(65) Prior Publication Data
US 2020/0113436 A1 Apr. 16, 2020

(30) Foreign Application Priority Data

May 1, 2017 (JP) .................................. 2017-091117

(51) Int. Cl.
*A61B 5/00* (2006.01)
*G16H 40/63* (2018.01)
*G16H 40/67* (2018.01)

(52) U.S. Cl.
CPC .......... *A61B 5/0024* (2013.01); *A61B 5/7495* (2013.01); *G16H 40/63* (2018.01);
(Continued)

(58) Field of Classification Search
CPC ... A61B 5/0024; A61B 5/7495; A61B 5/0006; A61B 5/0008; A61B 5/318;
(Continued)

(56) References Cited

U.S. PATENT DOCUMENTS

2005/0101844 A1 5/2005 Duckert et al.
2010/0327063 A1 12/2010 Medina et al.
(Continued)

FOREIGN PATENT DOCUMENTS

JP 2013-156919 A 8/2013
JP 2013156919 A * 8/2013
(Continued)

OTHER PUBLICATIONS

Habib et al, A novel authentication framework based on biometric and radio fingerprinting for the IoT in eHealth, SMART 2014 : The Third International Conference on Smart Systems, Devices and Technologies (Year: 2014).*

(Continued)

*Primary Examiner* — Joseph M Dietrich
*Assistant Examiner* — Ranjani Mari Sundaresan
(74) *Attorney, Agent, or Firm* — Sughrue Mion, PLLC

(57) ABSTRACT

A physiological information transmission method includes: by an information processing apparatus: acquiring sensor identification information of a physiological information detection sensor which is adapted to be attached to a living body, and living body identification information of the living body; and transmitting first association information associating the acquired sensor identification information and the acquired living body identification information, with each (Continued)

other; and by the physiological information detection sensor: receiving the first association information; determining whether or not the received first association information contains sensor identification information of the own sensor; and when the received first association information contains the sensor identification information of the own sensor, transmitting second association information associating the living body identification information in the received first association information, and physiological information which is detected by the physiological information detection sensor, with each other, to an outside of the own sensor.

10 Claims, 15 Drawing Sheets

(52) U.S. Cl.
CPC ............ *G16H 40/67* (2018.01); *A61B 5/0006* (2013.01); *A61B 5/0008* (2013.01)

(58) Field of Classification Search
CPC ... A61B 5/6833; A61B 5/02055; A61B 5/117; G16H 40/67; G16H 40/63
See application file for complete search history.

(56) References Cited

U.S. PATENT DOCUMENTS

| | | |
|---|---|---|
| 2012/0310669 A1 | 12/2012 | Carlberg et al. |
| 2013/0294969 A1* | 11/2013 | Chen .......................... A61L 2/18 422/28 |

FOREIGN PATENT DOCUMENTS

| | | |
|---|---|---|
| JP | 2014-68718 A | 4/2014 |
| WO | 2006/126107 A1 | 11/2006 |

OTHER PUBLICATIONS

International Search Report (PCT/ISA/210) dated Jul. 16, 2018 by the International Searching Authority in counterpart International Patent Application No. PCT/JP2018/016778.

Written Opinion (PCT/ISA/237) dated Jul. 16, 2018 by the International Searching Authority in counterpart International Patent Application No. PCT/JP2018/016778.

* cited by examiner

PHYSIOLOGICAL INFORMATION TRANSMISSION SYSTEM, PHYSIOLOGICAL INFORMATION DETECTION SENSOR, INFORMATION PROCESSING APPARATUS, AND PHYSIOLOGICAL INFORMATION TRANSMISSION METHOD

TECHNICAL FIELD

The present invention relates to a physiological information transmission system, a physiological information detection sensor, an information processing apparatus, and a physiological information transmission method.

BACKGROUND ART

In the field of medical equipment, conventionally, a physiological information detection sensor (medical telemeter) which detects physiological information such as an electrocardiogram, and which wirelessly transmits the detected physiological information is known (for example, PTL 1).

CITATION LIST

Patent Literature

[PTL 1] JP-A-2014-68718

SUMMARY OF INVENTION

Technical Problem

In the physiological information detection sensor disclosed in PTL 1, however, there is a problem in that it is impossible to easily know the person from whom the physiological information that is wirelessly transmitted by the physiological information detection sensor originates.

The invention has been conducted in view of the above circumstances. It is an object of the invention to provide a physiological information transmission system, physiological information detection sensor, information processing apparatus, and physiological information transmission method in which it is possible to easily know the person from whom physiological information that is wirelessly transmitted by a physiological information detection sensor originates.

Solution to Problem

In order to achieve the above object, according to an aspect of the invention, there is provided a physiological information transmission system comprising at least one physiological information detection sensor and an information processing apparatus, wherein the information processing apparatus includes: a sensor identification information acquiring section which is configured to acquire sensor identification information of the physiological information detection sensor; a living body identification information acquiring section which is configured to acquire living body identification information of a living body; and a first transmitter which is configured to transmit first association information associating the sensor identification information which is acquired by the sensor identification information acquiring section, and the living body identification information of the living body which is acquired by the living body identification information acquiring section, with each other, to the physiological information detection sensor, and the physiological information detection sensor includes: a physiological information detector which is configured to detect physiological information of the living body; a storage section which is configured to store the sensor identification information of the own sensor; a receiver which is configured to receive the first association information which is transmitted by the first transmitter of the information processing apparatus; a determining section which is configured to determine whether or not the first association information received by the receiver contains the sensor identification information of the own sensor which is stored in the storage section; and a second transmitter which, when the first association information received by the receiver contains the sensor identification information of the own sensor which is stored in the storage section, is configured to transmit second association information associating the living body identification information in the received first association information, and the physiological information of the living body which is detected by the physiological information detector, with each other, to an outside of the own sensor.

According to the aspect, a physiological information transmission system in which it is possible to easily know the person from whom the physiological information that is wirelessly transmitted by the physiological information detection sensor originates can be provided.

This is because, first, the information processing apparatus acquires the sensor identification information of the physiological information detection sensor, and the living body identification information, and transmits the first association information associating the sensor identification information and living body identification information which are acquired, with each other. Secondly, the physiological information detection sensor receives the first association information (the sensor identification information and the living body identification information) which is transmitted by the information processing apparatus, and determines whether the received first association information (the sensor identification information and the living body identification information) contains the sensor identification information of the own sensor or not. If the received first association information (the sensor identification information and the living body identification information) contains the sensor identification information of the own sensor, the physiological information detection sensor transmits, to the outside of the own sensor, the second association information associating the living body identification information associated with the sensor identification information of the own sensor in the received first association information (the sensor identification information and the living body identification information), and the physiological information which is detected by the physiological information detection sensor, with each other.

That is, the physiological information detection sensor transmits the physiological information detected by the physiological information detection sensor, as the second association information associated with the living body identification information, and therefore the party which receives the second association information can easily know the person from whom the received physiological information originates.

DESCRIPTION OF EMBODIMENTS

Figure 1:
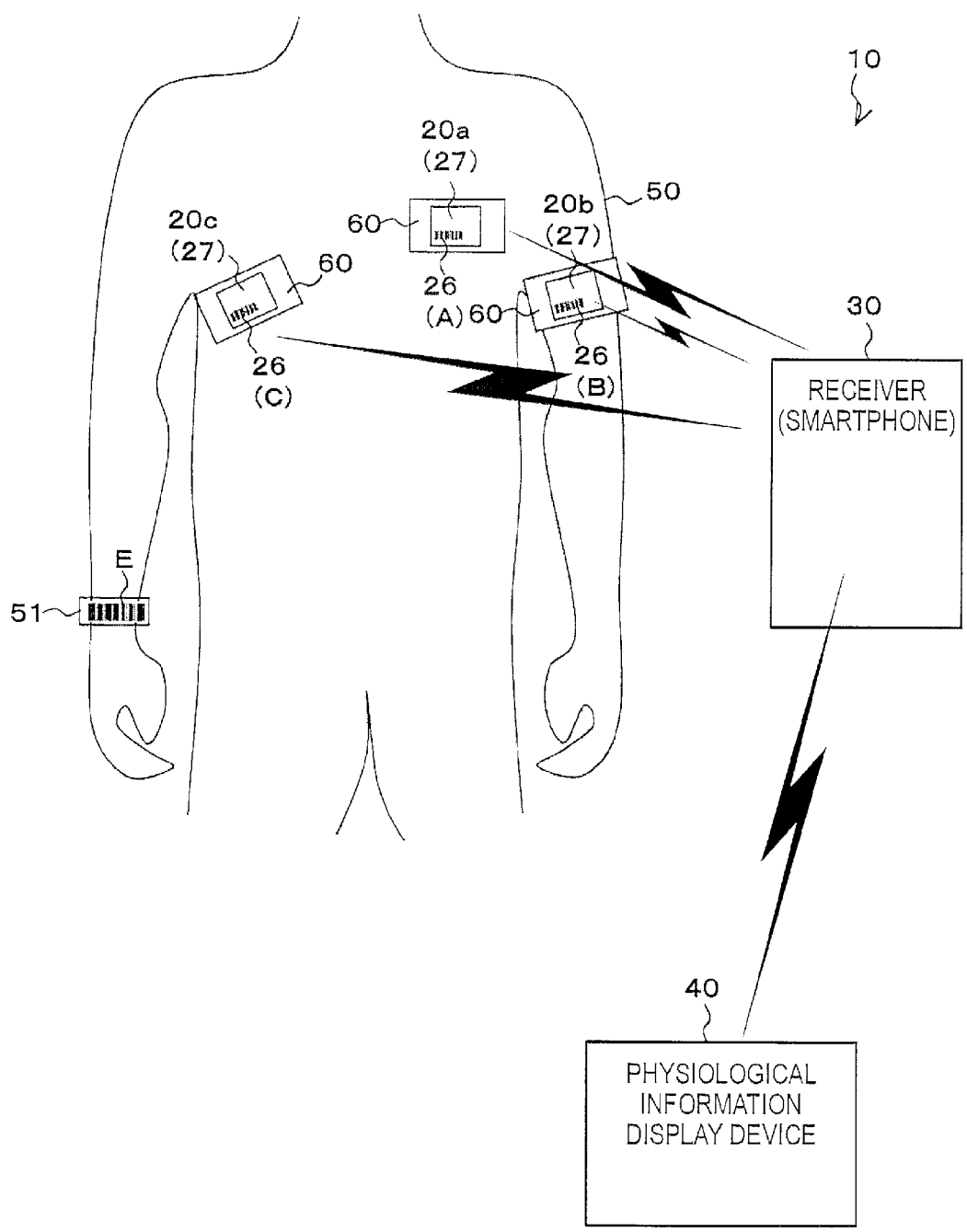
FIG. 1 is a schematic configuration diagram of a medical telemeter system 10.

Hereinafter, a medical telemeter system 10 which is an embodiment of the invention will be described with reference to the accompanying drawings. Corresponding components in the figures are denoted by the same reference numerals, and duplicated descriptions will be omitted.

[Outline of Medical Telemeter System 10]

FIG. 1 is a schematic configuration diagram of the medical telemeter system 10.

As shown in FIG. 1, a physiological information transmission system (hereinafter, referred to as the medical telemeter system 10) includes physiological information detection sensors 20a to 20c, an information processing apparatus (hereinafter, referred to as the receiver 30), a physiological information display device 40, etc.

The physiological information detection sensor 20a is attached to a pad 60 which is pasted to a living body (hereinafter, referred to as the patient 50), measures an electrocardiogram as physiological information of the patient 50, and wirelessly transmits the measured electrocardiogram (electrocardiogram data) to the receiver 30. The physiological information detection sensor 20b is attached to another pad 60 which is pasted to the patient 50, measures the NIBP (Non-Invasive Blood Pressure) as physiological information of the patient, and wirelessly transmits the measured NIBP (NIBP data) to the receiver 30. The physiological information detection sensor 20c is attached to a further pad 60 which is pasted to the patient 50, measures the TEMP (body temperature) as physiological information of the patient, and wirelessly transmits the measured body temperature (body temperature data) to the receiver 30. In the case where the physiological information detection sensors 20a to 20c are not particularly distinguished from one another, the sensors will be hereinafter referred to as the physiological information detection sensor 20.

For example, the receiver 30 is a smartphone, receives the physiological information which is wirelessly transmitted by the physiological information detection sensor 20, and displays the received physiological information on a display (not shown) that is provided in the receiver 30. Alternatively, the receiver wirelessly transmits (transfers) the received physiological information to the physiological information display device 40. The receiver 30 is not limited to a smartphone as far as the receiver is a device which can receive the physiological information that is wirelessly transmitted from the physiological information detection sensor 20, and which can wirelessly transmit the received physiological information to the physiological information display device 40.

The physiological information display device 40 receives the physiological information which is transmitted by the receiver 30, and displays the received physiological information on a display (not shown) that is provided in the physiological information display device 40.

[Physiological Information Detection Sensor]

Figure 2A:
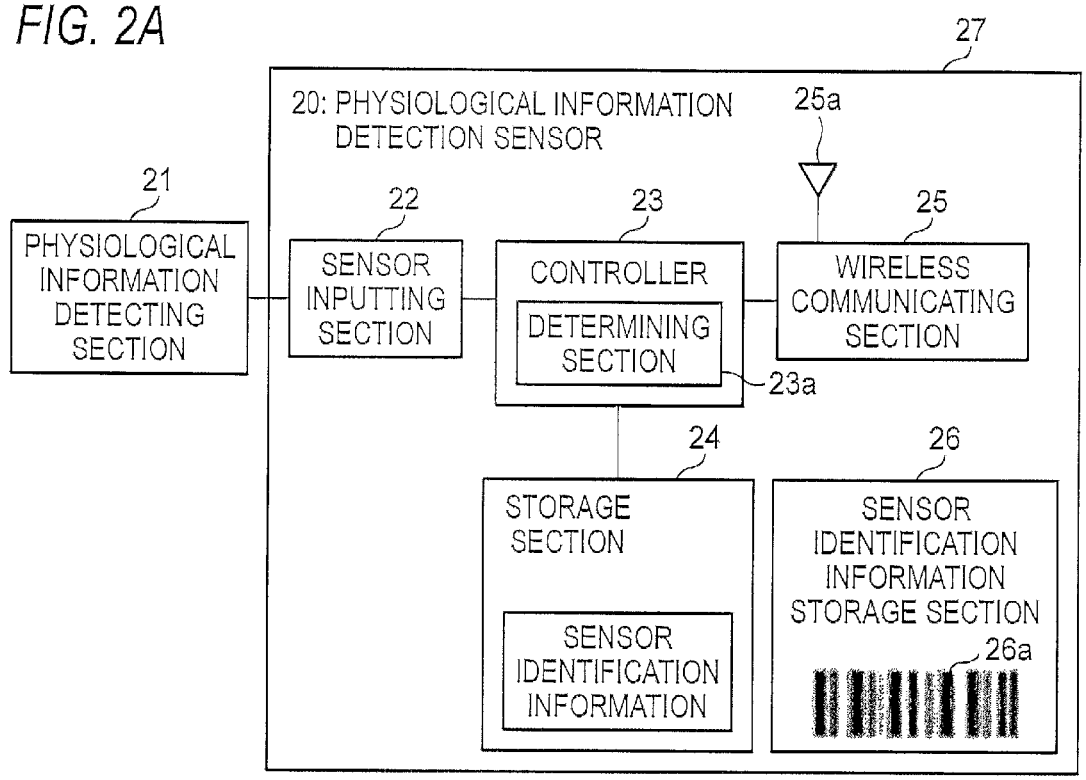
FIG. 2A is a schematic hardware diagram of a physiological information detection sensor 20.

Next, the physiological information detection sensor 20 will be described. FIG. 2A is a schematic hardware diagram of the physiological information detection sensor 20.

Figure 2B:
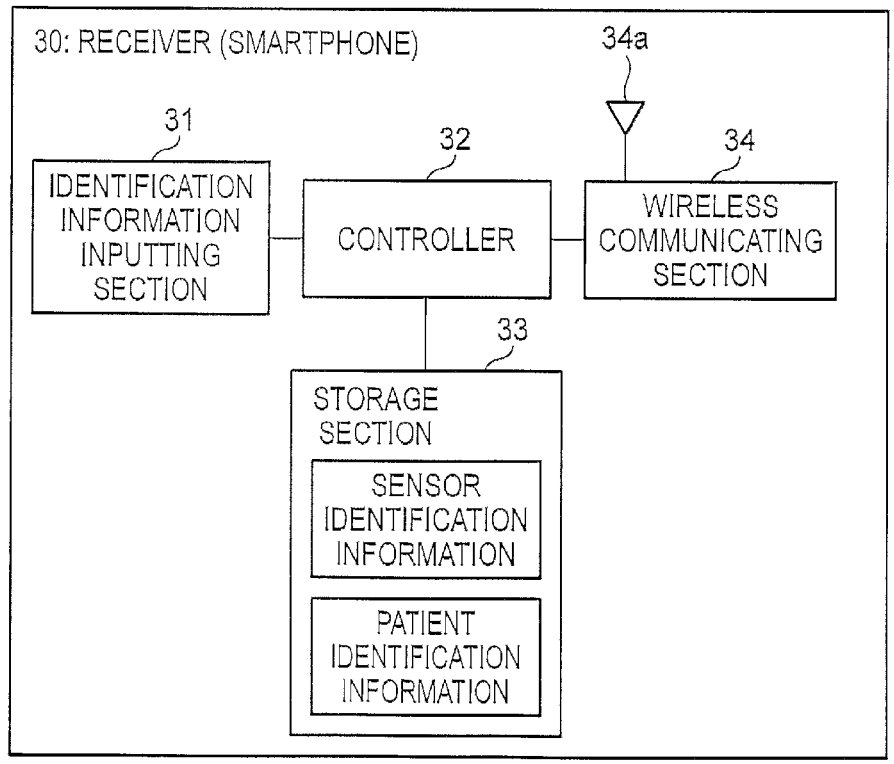
FIG. 2B is a schematic hardware diagram of a receiver 30.

As shown in FIG. 2B, the physiological information detection sensor 20 includes a physiological information detector 21, a sensor inputting section 22, a controller 23, a storage section 24, a wireless communicating section 25, a sensor identification information recording section 26, and a case 27.

The physiological information detector 21 detects physiological information (or a physiological signal) of the patient 50. For example, the physiological information detector 21 of the physiological information detection sensor 20a is configured by three lead electrodes (R, L, F), and detects an electrocardiogram as physiological information (or a physiological signal) of the patient 50. Moreover, the physiological information detector 21 of the physiological information detection sensor 20b is an NIBP sensor, and detects the NIBP as physiological information (or a physiological signal) of the patient 50. Moreover, the physiological information detector 21 of the physiological information detection sensor 20c is a temperature sensor, and detects the body temperature (TEMP) as physiological information (or a physiological signal) of the patient 50.

The sensor inputting section 22 applies amplification, A/D conversion, and the like on the physiological information of the patient 50 which is detected by the physiological information detector 21, and then supplies the resulting data to the controller 23.

The controller 23 includes a CPU and a RAM. The CPU of the physiological information detection sensor 20 controls various hardware devices (for example, the wireless communicating section 25) constituting the physiological information detection sensor 20, by executing predetermined programs. For example, the CPU of the physiological information detection sensor 20 transmits physiological information (for example, electrocardiogram data) which is converted by an A/D converter, to the receiver 30 through the wireless communicating section 25. When the CPU of the physiological information detection sensor 20 executes a predetermined program, moreover, the CPU functions as a determining section 23a which determines whether or not the first association information received by the wireless communicating section 25 contains the sensor identification information of the own sensor that is stored in the storage section 24.

Figure 5:
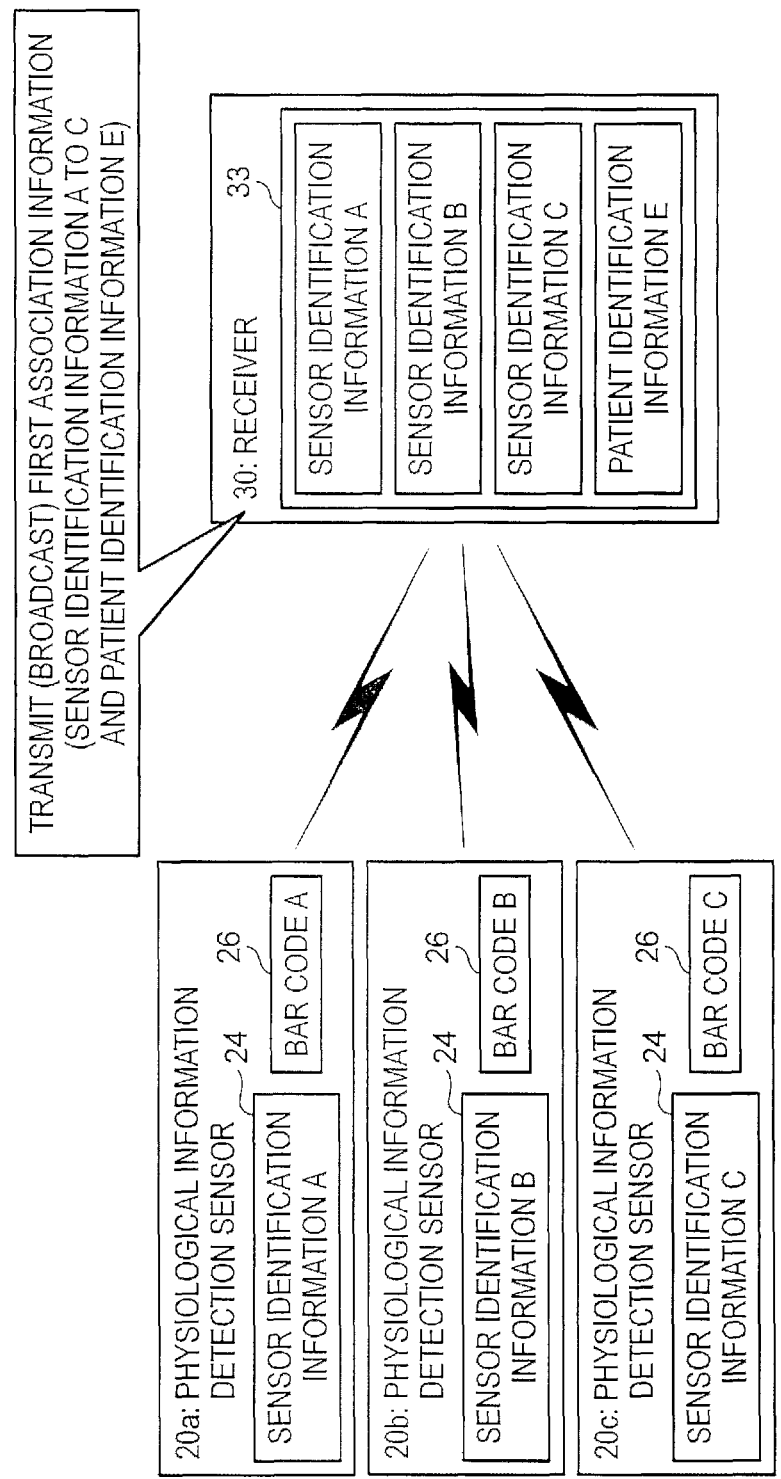
FIG. 5 is a diagram showing a manner in which the receiver 30 transmits (broadcasts) first association information (sensor identification information A to C and patient identification information E) to physiological information detection sensors 20.

For example, the storage section 24 is a rewritable nonvolatile memory such as a flash ROM, and previously stores the sensor identification information of the own sensor. As shown in FIG. 5, for example, the storage section 24 of the physiological information detection sensor 20a previously stores the sensor identification information (hereinafter, referred to as sensor identification information A) of the physiological information detection sensor 20a. Moreover, the storage section 24 of the physiological information detection sensor 20b previously stores the sensor identification information (hereinafter, referred to as sensor identification information B) of the physiological information detection sensor 20b. Furthermore, the storage section 24 of the physiological information detection sensor 20c previously stores the sensor identification information (hereinafter, referred to as sensor identification information C) of the physiological information detection sensor 20c.

For example, the wireless communicating section 25 is a communication module (e.g., a BLE module) compatible to BLE (Bluetooth Low Energy) technology, and wirelessly communicates with another BLE compatible device (e.g., the receiver 30) in a short range (e.g., 100 mm) through an antenna 25a. The wireless communicating section 25 corresponds to the receiver and second transmitter in the invention.

As shown in FIG. 1, for example, the sensor identification information recording section 26 is disposed in the case 27. A bar code indicating the sensor identification information identical with the sensor identification information of the own sensor which is stored in the storage section 24 is recorded on the sensor identification information storage section 26. As shown in FIG. 5, for example, a bar code (hereinafter, referred to as the bar code A) indicating the sensor identification information identical with the sensor identification information A of the physiological information detection sensor 20a is recorded on the sensor identification information recording section 26 of the physiological information detection sensor 20a. Moreover, a bar code (hereinafter, referred to as the bar code B) indicating the sensor identification information identical with the sensor identification information B of the physiological information detection sensor 20b is recorded on the sensor identification information recording section 26 of the physiological information detection sensor 20b. Furthermore, a bar code (hereinafter, referred to as the bar code C) indicating the sensor identification information identical with the sensor identification information C of the physiological information detection sensor 20c is recorded on the sensor identification information recording section 26 of the physiological information detection sensor 20c.

Specifically, the sensor identification information recording section 26 is a display surface of a seal which is pasted to the case 27, an electronic paper sheet, or the like. The bar codes A to C are displayed on display surfaces of seals, electronic paper sheets, or the like which are pasted to the cases 27, respectively.

For example, the case 27 is a rectangular box-like case, and accommodates the sensor inputting section 22, the controller 23, the storage section 24, and the wireless communicating section 25.

[Receiver]

Next, the receiver 30 will be described. FIG. 2B is a schematic hardware diagram of the receiver 30.

As shown in FIG. 2B, the receiver 30 includes an identification information inputting section 31, a controller 32, a storage section 33, and a wireless communicating section 34.

The identification information inputting section 31 is means for optically reading a bar code (hereinafter, referred to as the bar code E) indicating living body identification information (hereinafter, referred to as the patient identification information E) of the patient 50 which is recorded on a wristband 51 attached to the patient 50, and the bar codes A to C which are recorded on the sensor identification information recording sections 26 of the physiological information detection sensors 20 attached to the patient 50. Although not illustrated, the identification information inputting section includes: a camera such as a CCD camera which takes images of the bar codes A to C, E; a bar code recognizing section which recognizes the bar codes A to C, E based on the taken images; an identification information detecting section which detects the sensor identification information A to C and patient identification information E that are indicated by the recognized bar codes; and the like. The sensor identification information A to C and patient identification information E which are detected by the identification information detecting section are supplied to the controller 32, and, as shown in FIG. 5, then stored in the storage section 33. For example, the bar code recognizing section and the identification information detecting section are realized by execution of predetermined programs which is performed by the CPU of the physiological information detection sensor 20. The identification information inputting section 31 corresponds to the sensor identification information acquiring section and living body identification information acquiring section in the invention.

The controller 32 includes a CPU and a ROM. The CPU of the receiver 30 controls various hardware devices (for example, the wireless communicating section 34) constituting the receiver 30, by executing predetermined programs. For example, the CPU of the receiver 30 transmits the first association information associating the sensor identification information and patient identification information which are supplied (acquired) from the identification information inputting section 31, with each other to the physiological information detection sensor 20 through the wireless communicating section 34.

The storage section 33 is configured by, for example, a RAM, and stores the sensor identification information and patient identification information which are supplied (acquired) from the identification information inputting section 31.

For example, the wireless communicating section 34 is a communication module (e.g., a BLE module) compatible to BLE (Bluetooth Low Energy) technology, and wirelessly communicates with another BLE compatible device (e.g., the physiological information detection sensor 20) in a short range (e.g., 100 mm) through an antenna 34a. The wireless communicating section 34 corresponds to the first transmitter in the invention.

Operation Example of Medical Telemeter System 10

Figure 3:
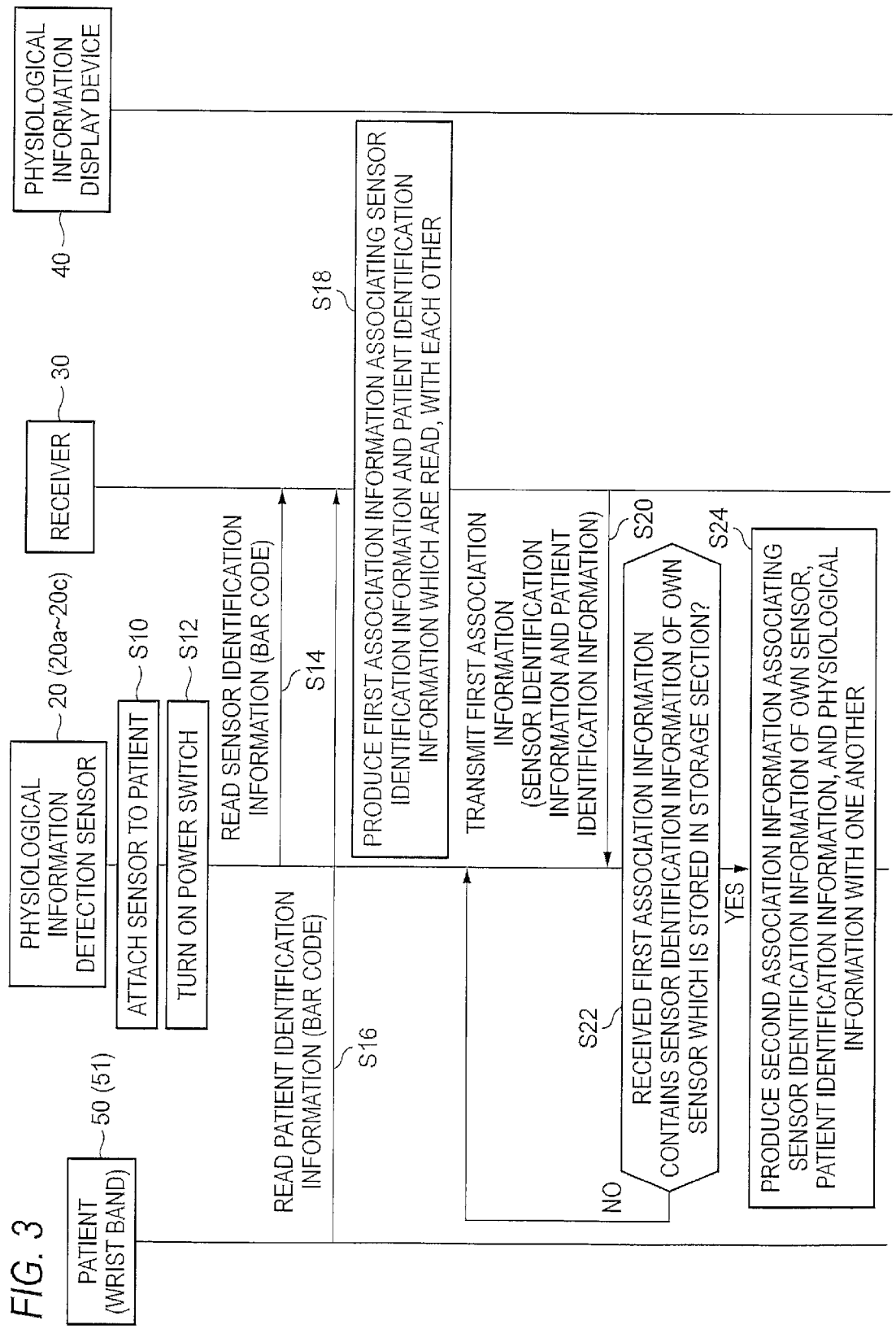
FIG. 3 is a sequence diagram illustrating an operation of the medical telemeter system 10.
Figure 4:
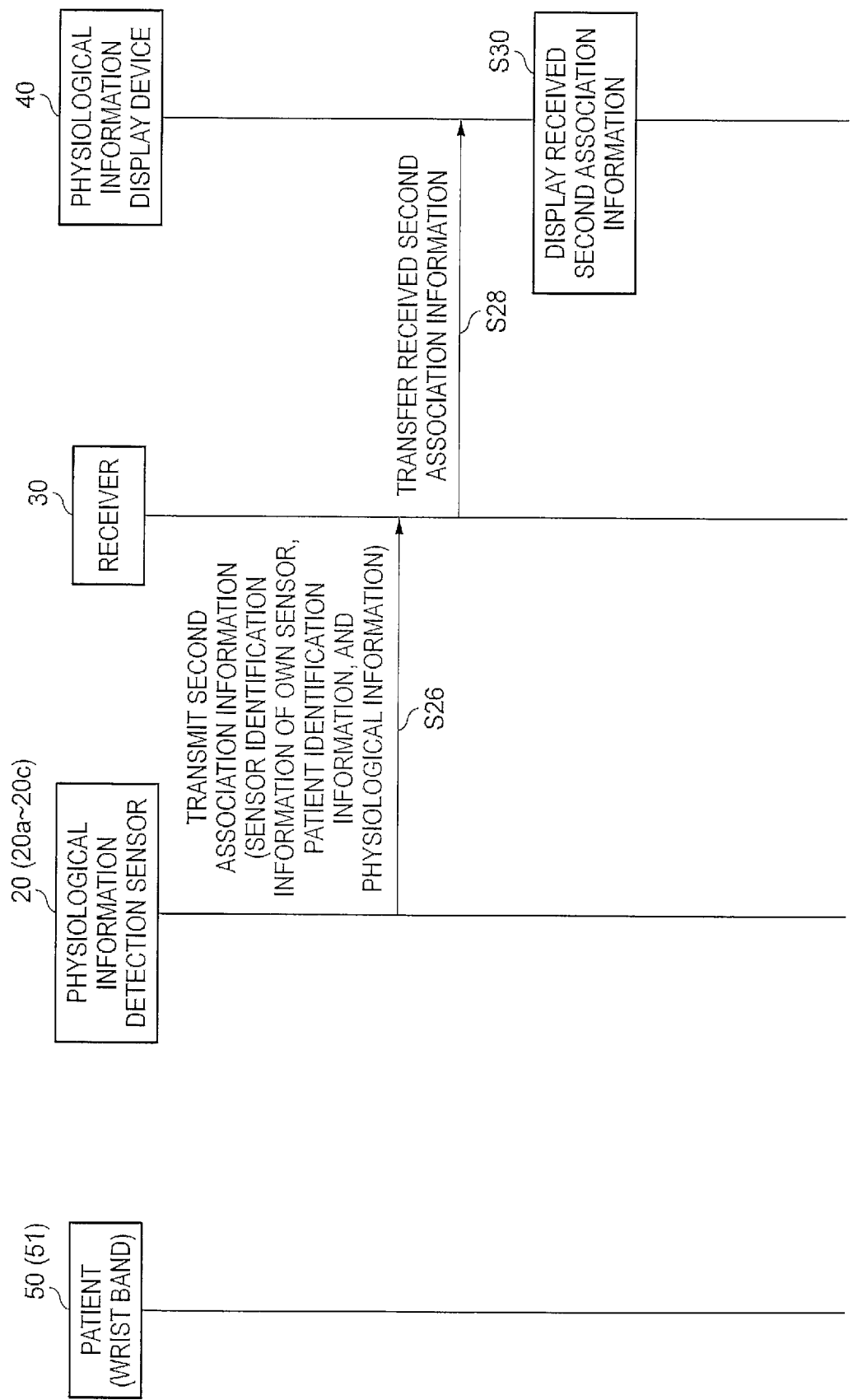
FIG. 4 is a sequence diagram illustrating the operation of the medical telemeter system 10.

Next, operation examples of the thus configured medical telemeter system 10 will be described. FIGS. 3 and 4 are sequence diagrams illustrating the operation of the medical telemeter system 10.

Operation Example in Case of One Patient

Hereinafter, an operation example in the case where one patient exists will be described with reference to FIGS. 3 and 4.

As shown in FIG. 1, first, the physiological information detection sensors 20a to 20c are attached to the patient 50 (step S10), and power switches (not shown) of the respective physiological information detection sensors 20a to 20c are turned ON (step S12). This causes the wireless communicating sections 25 of the respective physiological information detection sensors 20a to 20c to enter a state of waiting for wireless communication from the receiver 30.

Next, the bar codes A to C which are recorded on the respective sensor identification information storage sections 26 of the physiological information detection sensors 20a to 20c attached to the patient 50 are read (step S14). Then, the bar code E which is recorded on the wristband 51 attached to the patient 50 is read (step S16). Specifically, images of the bar codes A to C which are recorded on the respective sensor identification information storage sections 26 of the physiological information detection sensors 20a to 20c, and the bar code E which is recorded on the wristband 51 attached to the patient 50 are sequentially taken by the camera such as a CCD camera disposed in the receiver 30. The bar code recognizing section recognizes the bar codes A to C, E based on the taken images. Then, the identification information detecting section detects the sensor identification information A to C and patient identification information E that are indicated by the recognized bar codes. The sensor identification information A to C and patient identification information E that are detected by the identification information detecting section are supplied to the controller 32, and then stored in the storage section 33 as shown in FIG. 5.

Next, the CPU of the receiver 30 reads out the sensor identification information A to C and the patient identification information E from the storage section 33, produces the first association information associating the sensor identification information A to C and the patient identification information E with each other (step S18), and, as shown in FIG. 5, transmits (for example, broadcasts or advertises) the produced first association information (the sensor identification information A to C and the patient identification information E) to the physiological information detection sensor 20 through the wireless communicating section 34 (step S20). FIG. 5 is a diagram showing a manner in which the receiver 30 transmits (broadcasts) the first association information (the sensor identification information A to C and the patient identification information E) to the physiological information detection sensor 20.

When the wireless communicating section 25 receives the first association information (the sensor identification information A to C and the patient identification information E), then, the CPU of the physiological information detection sensor 20 causes the received first association information (the sensor identification information A to C and the patient identification information E) to be stored in the storage section 24 or the like of the physiological information detection sensor 20. The CPU (the determining section 23a) of the physiological information detection sensor 20 determines whether or not the received first association information (the sensor identification information A to C and the patient identification information E) contains the sensor identification information of the own sensor which is previously stored in the storage section 24 (step S22).

If the CPU of the physiological information detection sensor 20 determines that the received first association information (the sensor identification information A to C and the patient identification information E) contains the sensor identification information of the own sensor which is previously stored in the storage section 24 (step S22: Yes), the CPU establishes connection with the receiver 30, reads out the sensor identification information of the own sensor, and the patient identification information associated with the sensor identification information of the own sensor from the storage section 24, produces the second association information associating the sensor identification information of the own sensor, the patient identification information, and the physiological information of the patient 50 which is detected by the physiological information detector 21, with one another (step S24), and transmits the produced second association information (the sensor identification information, the patient identification information, and the physiological information of the patient 50) to the receiver 30 through the wireless communicating section 25 (step S26).

Figure 6:
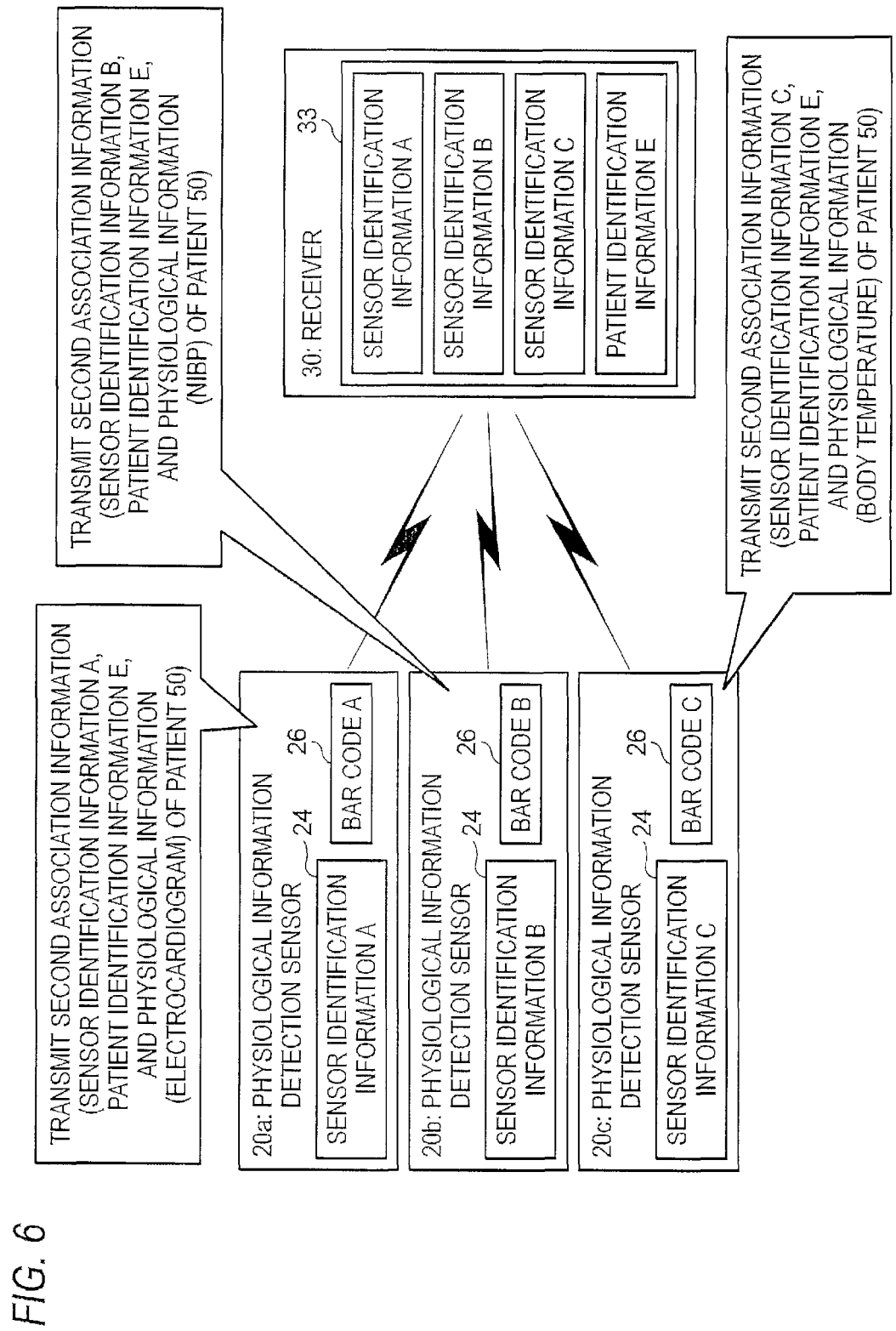
FIG. 6 is a diagram showing a manner in which the physiological information detection sensors 20 transmit second association information (the sensor identification information, the patient identification information, and physiological information of a patient 50).

If the CPU of the physiological information detection sensor 20a determines that the received first association information (the sensor identification information A to C and the patient identification information E) contains the sensor identification information A of the own sensor which is stored in the storage section 24 (step S22: Yes), for example, the CPU establishes connection with the receiver 30, reads out the sensor identification information A of the own sensor, and the patient identification information E associated with the sensor identification information of the own sensor from the storage section 24, produces the second association information associating the sensor identification information A of the own sensor, the patient identification information E, and the physiological information (electrocardiogram data) of the patient 50 which is detected by the physiological information detector 21, with one another (step S24), and, as shown in FIG. 6, transmits the produced second association information (the sensor identification information A, the patient identification information E, and the physiological information (electrocardiogram data) of the patient 50) to the receiver 30 through the wireless communicating section 25 (step S26). FIG. 6 is a diagram showing a manner in which the physiological information detection sensor 20 transmits the second association information (the sensor identification information, the patient identification information, and the physiological information of the patient 50).

If the CPU of the physiological information detection sensor 20b determines that the received first association information (the sensor identification information A to C and the patient identification information E) contains the sensor identification information B of the own sensor which is stored in the storage section 24 (step S22: Yes), similarly, the CPU establishes connection with the receiver 30, reads out the sensor identification information B of the own sensor, and the patient identification information E associated with the sensor identification information of the own sensor from the storage section 24, produces the second association information associating the sensor identification information B of the own sensor, the patient identification information E, and the physiological information (NIBP data) of the patient 50 which is detected by the physiological information detector 21, with one another (step S24), and, as shown in FIG. 6, transmits the produced second association information (the sensor identification information B, the patient identification information E, and the physiological information (NIBP data) of the patient 50) to the receiver 30 through the wireless communicating section 25 (step S26).

If the CPU of the physiological information detection sensor 20c determines that the received first association information (the sensor identification information A to C and the patient identification information E) contains the sensor identification information C of the own sensor which is stored in the storage section 24 (step S22: Yes), similarly, the CPU establishes connection with the receiver 30, reads out the sensor identification information C of the own sensor, and the patient identification information E associated with the sensor identification information of the own sensor from the storage section 24, produces the second association information associating the sensor identification information C of the own sensor, the patient identification information E, and the physiological information (body temperature data) of the patient 50 which is detected by the physiological information detector 21, with one another (step S24), and, as shown in FIG. 6, transmits the produced second association information (the sensor identification information C, the patient identification information E, and the physiological information (body temperature data) of the patient 50) to the receiver 30 (or the physiological information displaying device 40) through the wireless communicating section 25 (step S26).

When the wireless communicating section 34 receives the second association information transmitted by the physiological information detection sensor 20, then, the receiver 30 transmits (transfers) the received second identification information to the physiological information display device 40 (step S28).

When the physiological information display device 40 receives the second association information transmitted by the receiver 30 (or the physiological information detection sensor 20), then, the device displays the received second association information (the sensor identification information, the patient identification information, and the physiological information of the patient 50) on the display provided in the physiological information display device 40 (step S30).

Figure 7:
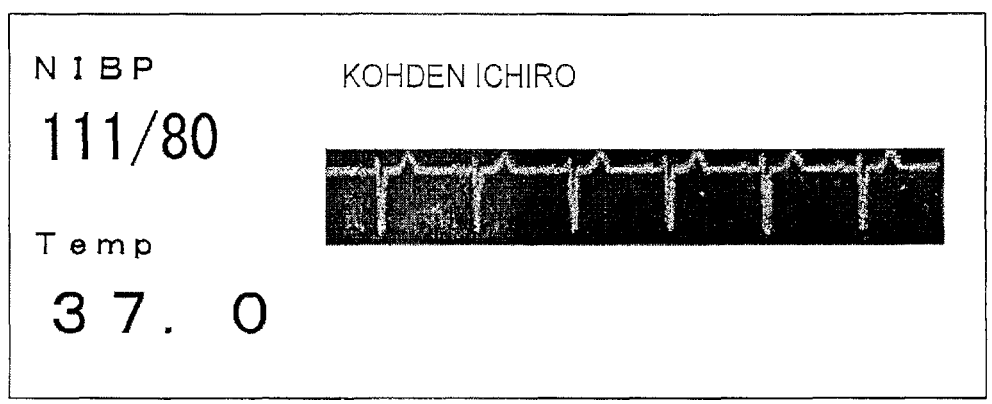
FIG. 7 is a view showing a display example of the second association information (the sensor identification information, the patient identification information, and the physiological information of the patient 50).

As shown in FIG. 7, for example, the patient name, the electrocardiogram, the NIBP, and the TEMP are displayed in a predetermined region of the display provided in the physiological information display device 40. FIG. 7 shows a display example of the second association information (the sensor identification information, the patient identification information, and the physiological information of the patient 50). For example, the patient name can be acquired by referring correspondence relationships between the patient identification information and the patient name, and held by an electronic medical chart (not shown).

According to the operation example, as described above, it is possible to provide a physiological information transmission system, physiological information detection sensor, information processing apparatus, and physiological information transmission method in which the person from whom the physiological information that is wirelessly transmitted by the physiological information detection sensor 20 originates can be easily known.

This is because, first, the receiver 30 acquires the sensor identification information A to C of the physiological information detection sensors 20 attached to the patient 50, and the patient identification information E of the patient 50, and transmits the first association information associating the sensor identification information A to C and patient identification information E which are acquired, with each other. Secondly, the physiological information detection sensor 20 receives the first association information (the sensor identification information A to C and the patient identification information E) which is transmitted by the receiver 30, and determines whether the received first association information (the sensor identification information A to C and the patient identification information E) contains the sensor identification information of the own sensor or not. If the received first association information (the sensor identification information A to C and the patient identification information E) contains the sensor identification information of the own sensor, the physiological information detection sensor transmits, to the outside of the own sensor, the second association information associating the patient identification information associated with the sensor identification information of the own sensor in the received first association information (the sensor identification information A to C and the patient identification information E), the sensor identification information of the own sensor, and the physiological information which is detected by the physiological information detection sensor 20, with one another.

That is, the physiological information detection sensor 20 transmits the physiological information of the patient 50 which is detected by the physiological information detection sensor 20, as the second association information associated with the sensor identification information of the own sensor and the patient identification information, and therefore the party (for example, the receiver 30) which receives the second association information can easily know the person from whom the received physiological information of the patient 50 originates.

Operation Example in Case of Plural Patients

Next, an operation example in the case where a plurality of (for example, three) patients exist will be described with reference to FIGS. 3 and 4.

Figure 8:
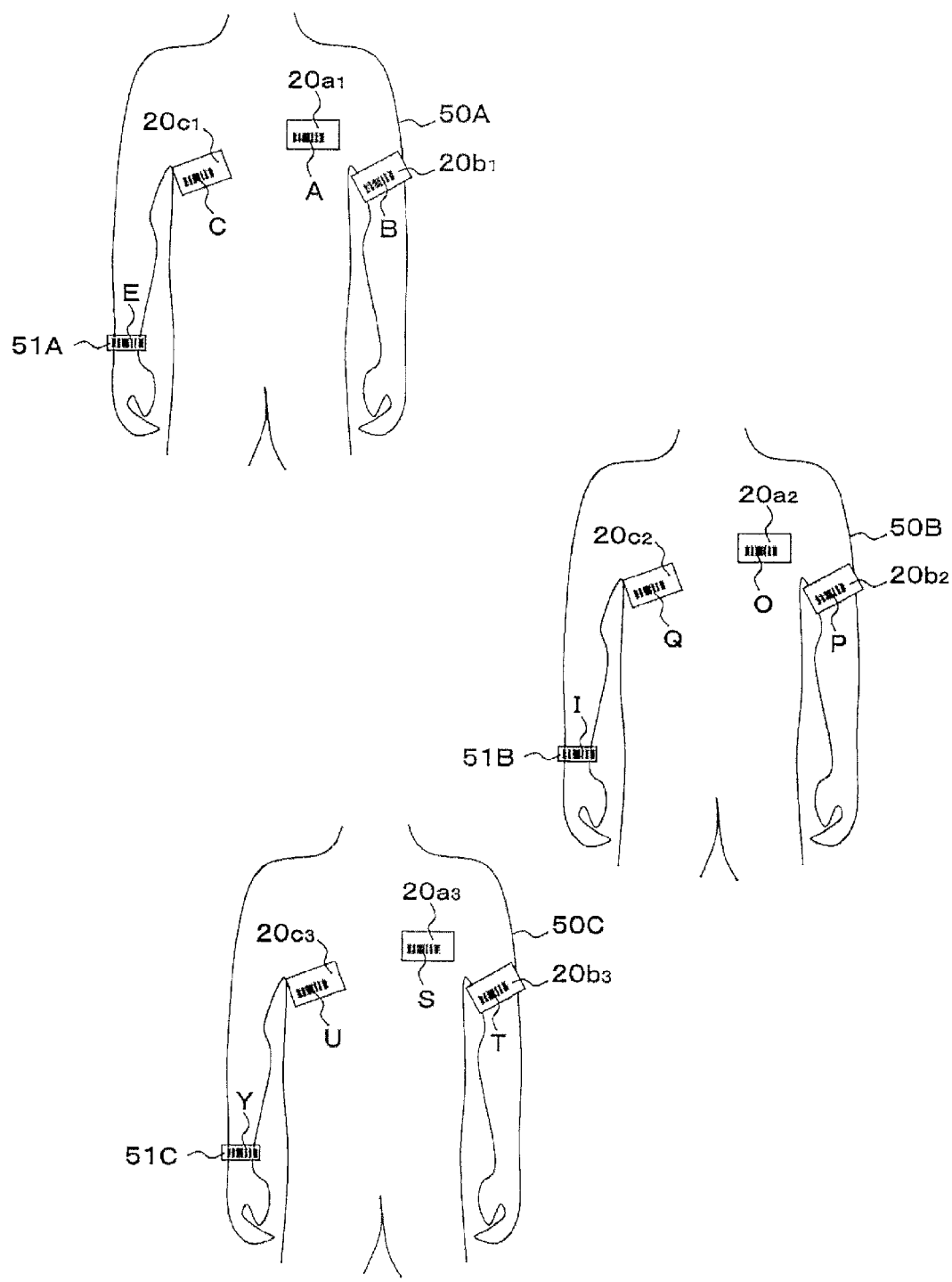
FIG. 8 is a diagram showing a state where physiological information detection sensors $20a_1$ to $20c_1$, $20a_2$ to $20c_2$, $20a_3$ to $20c_3$ are attached to a plurality of patients 50A to 50C, respectively.

FIG. 8 is a diagram showing a state where physiological information detection sensors $20a_1$ to $20c_1$, $20a_2$ to $20c_2$, $20a_3$ to $20c_3$ are attached to a plurality of patients 50A to 50C, respectively.

As shown in FIG. 8, first, the physiological information detection sensors $20a_1$ to $20c_1$ are attached to the patient 50A, the physiological information detection sensors $20a_2$ to $20c_2$ are attached to the patient 50B, and the physiological information detection sensors $20a_3$ to $20c_3$ are attached to the patient 50C (step S10), and power switches (not shown) of the respective physiological information detection sensors $20a_1$ to $20c_1$, $20a_2$ to $20c_2$, $20a_3$ to $20c_3$ are turned ON (step S12). This causes the wireless communicating sections 25 of the respective physiological information detection sensors $20a_1$ to $20c_1$, $20a_2$ to $20c_2$, $20a_3$ to $20c_3$ to enter a state of waiting for wireless communication from the receiver 30.

Figure 9:
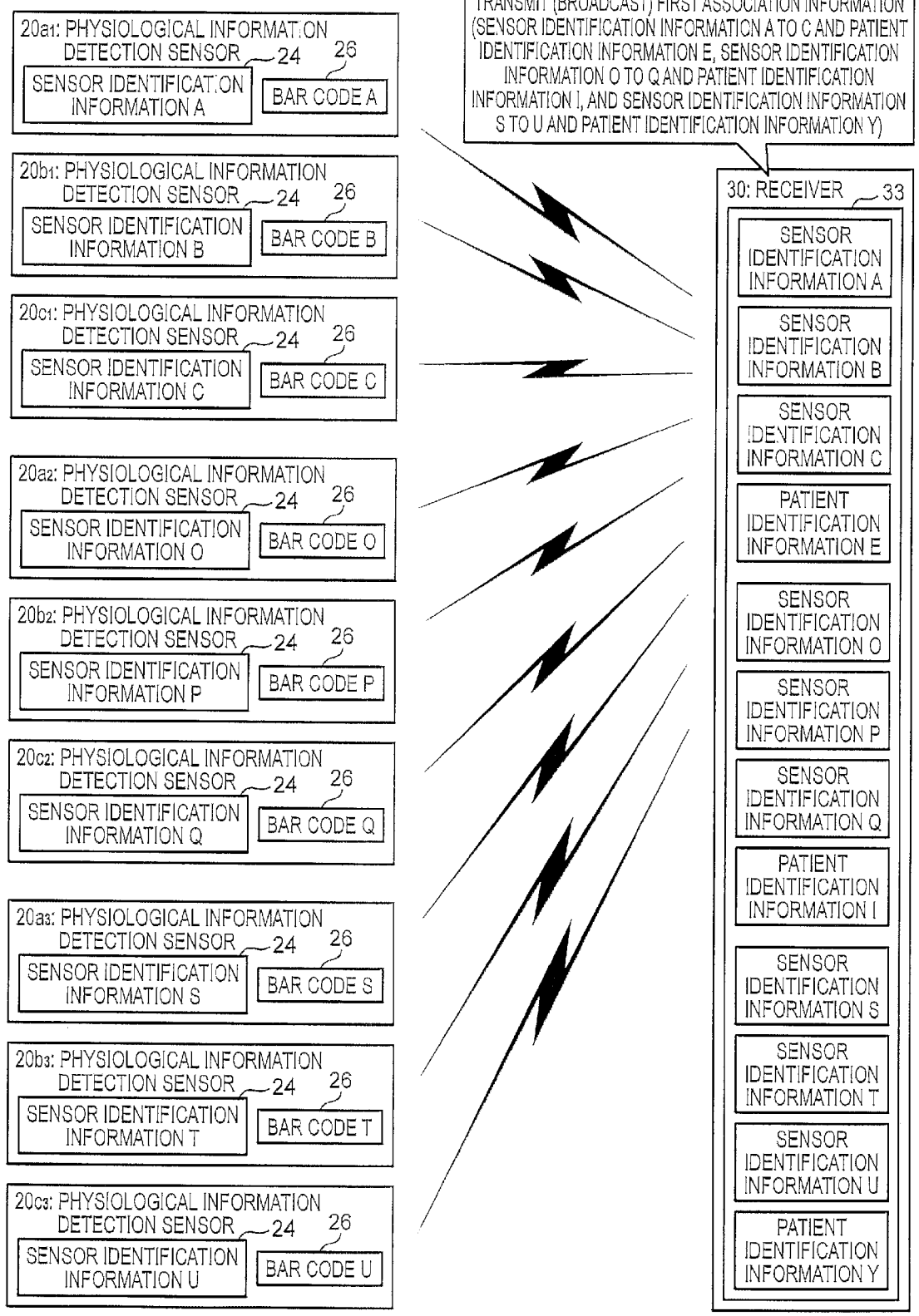
FIG. 9 is a diagram showing a manner in which the receiver 30 transmits (broadcasts) first association information (the sensor identification information A to C and the patient identification information E, sensor identification information O to Q and patient identification information I, and sensor identification information S to U and patient identification information Y) to the physiological information detection sensors 20.

FIG. 9 is a diagram showing a manner in which the receiver 30 transmits (broadcasts) the first association information (the sensor identification information A to C and the patient identification information E, the sensor identification information O to Q and the patient identification information I, and sensor identification information S to U and the patient identification information Y) to the physiological information detection sensors 20.

As shown in FIG. 9, the storage section 24 of the physiological information detection sensor $20a_1$ previously stores the sensor identification information (hereinafter, referred to as the sensor identification information A) of the physiological information detection sensor $20a_1$. Moreover, the storage section 24 of the physiological information detection sensor $20b_1$ previously stores the sensor identification information (hereinafter, referred to as the sensor identification information B) of the physiological information detection sensor $20b_1$. Furthermore, the storage section 24 of the physiological information detection sensor $20c_1$ previously stores the sensor identification information (hereinafter, referred to as the sensor identification information C) of the physiological information detection sensor $20c_1$.

Moreover, the storage section 24 of the physiological information detection sensor $20a_2$ previously stores the sensor identification information (hereinafter, referred to as the sensor identification information O) of the physiological information detection sensor $20a_2$. Moreover, the storage section 24 of the physiological information detection sensor $20b_2$ previously stores the sensor identification information (hereinafter, referred to as the sensor identification information P) of the physiological information detection sensor $20b_2$. Furthermore, the storage section 24 of the physiological information detection sensor $20c_2$ previously stores the sensor identification information (hereinafter, referred to as the sensor identification information Q) of the physiological information detection sensor $20c_2$.

Moreover, the storage section 24 of the physiological information detection sensor $20a_3$ previously stores the sensor identification information (hereinafter, referred to as the sensor identification information S) of the physiological information detection sensor $20a_3$. Moreover, the storage section 24 of the physiological information detection sensor $20b_3$ previously stores the sensor identification information (hereinafter, referred to as the sensor identification information T) of the physiological information detection sensor $20b_3$. Furthermore, the storage section 24 of the physiological information detection sensor $20c_3$ previously stores the sensor identification information (hereinafter, referred to as the sensor identification information U) of the physiological information detection sensor $20c_3$.

As shown in FIG. 9, moreover, a bar code (hereinafter, referred to as the bar code A) indicating the sensor identification information identical with the sensor identification information A of the physiological information detection sensor $20a_1$ is recorded on the sensor identification information recording section 26 of the physiological information detection sensor $20a_1$. Moreover, a bar code (hereinafter, referred to as the bar code B) indicating the sensor identification information identical with the sensor identification information B of the physiological information detection sensor $20b_1$ is recorded on the sensor identification information recording section 26 of the physiological information detection sensor $20b_1$. Furthermore, a bar code (hereinafter, referred to as the bar code C) indicating the sensor identification information identical with the sensor identification information C of the physiological information detection sensor $20c_1$ is recorded on the sensor identification information recording section 26 of the physiological information detection sensor $20c_1$.

Moreover, a bar code (hereinafter, referred to as the bar code O) indicating the sensor identification information identical with the sensor identification information O of the physiological information detection sensor $20a_2$ is recorded on the sensor identification information recording section 26 of the physiological information detection sensor $20a_2$. Moreover, a bar code (hereinafter, referred to as the bar code P) indicating the sensor identification information identical with the sensor identification information P of the physiological information detection sensor $20b_2$ is recorded on the sensor identification information recording section 26 of the physiological information detection sensor $20b_2$. Furthermore, a bar code (hereinafter, referred to as the bar code Q) indicating the sensor identification information identical with the sensor identification information Q of the physiological information detection sensor $20c_2$ is recorded on the sensor identification information recording section 26 of the physiological information detection sensor $20c_2$.

Moreover, a bar code (hereinafter, referred to as the bar code S) indicating the sensor identification information identical with the sensor identification information S of the physiological information detection sensor $20a_3$ is recorded on the sensor identification information recording section 26 of the physiological information detection sensor $20a_3$. Moreover, the sensor identification information recording section 26 of the physiological information detection sensor $20b_3$ records a bar code (hereinafter, referred to as the bar code T) indicating the sensor identification information identical with the sensor identification information T of the physiological information detection sensor $20b_3$. Furthermore, the sensor identification information recording section 26 of the physiological information detection sensor $20c_3$ records a bar code (hereinafter, referred to as the bar code U) indicating the sensor identification information identical with the sensor identification information U of the physiological information detection sensor $20c_3$.

In the case where the physiological information detection sensors $20a_1$ to $20c_1$, $20a_2$ to $20c_2$, $20a_3$ to $20c_3$ are not particularly distinguished from one another, the sensors will be hereinafter referred to as the physiological information detection sensors 20a to 20c.

Next, the bar codes A to C which are recorded on the respective sensor identification information storage sections 26 of the physiological information detection sensors $20a_1$ to $20c_1$ attached to the patient 50A are read (step S14). Then, the bar code E which is recorded on a wristband 51A attached to the patient 50A is read (step S16). Specifically, images of the bar codes A to C which are recorded on the respective sensor identification information storage sections 26 of the physiological information detection sensors $20a_1$ to $20c_1$, and the bar code E which is recorded on the wristband 51A attached to the patient 50A are sequentially taken by the camera such as a CCD camera disposed in the receiver 30. The bar code recognizing section recognizes the bar codes A to C, E based on the taken images. Then, the identification information detecting section detects the sensor identification information A to C and patient identification information E that are indicated by the recognized bar codes. The sensor identification information A to C and patient identification information E that are detected by the identification information detecting section are supplied to the controller 32, and then stored in the storage section 33 as shown in FIG. 9.

Next, the bar codes O to Q which are recorded on the respective sensor identification information storage sections 26 of the physiological information detection sensors $20a_2$ to $20c_2$ attached to the patient 50B are read (step S14). Then, a bar code I which is recorded on a wristband 51B attached to the patient 50B is read (step S16). Specifically, images of the bar codes O to Q which are recorded on the respective sensor identification information storage sections 26 of the physiological information detection sensors $20a_2$ to $20c_2$, and the bar code I which is recorded on the wristband 51B attached to the patient 50B are sequentially taken by the camera such as a CCD camera disposed in the receiver 30. The bar code recognizing section recognizes the bar codes O to Q, I based on the taken images. Then, the identification information detecting section detects the sensor identification information O to Q and patient identification information I that are indicated by the recognized bar codes. The sensor identification information O to Q and patient identification information I that are detected by the identification information detecting section are supplied to the controller 32, and then stored in the storage section 33 as shown in FIG. 9.

Next, the bar codes S to U which are recorded on the respective sensor identification information storage sections 26 of the physiological information detection sensors $20a_3$ to $20c_3$ attached to the patient 50C are read (step S14). Then, a bar code Y which is recorded on a wristband 51C attached to the patient 50C is read (step S16). Specifically, images of the bar codes S to U which are recorded on the respective sensor identification information storage sections 26 of the physiological information detection sensors $20a_3$ to $20c_3$, and the bar code Y which is recorded on the wristband 51C attached to the patient 50C are sequentially taken by the camera such as a CCD camera disposed in the receiver 30. The bar code recognizing section recognizes the bar codes S to U, Y based on the taken images. Then, the identification information detecting section detects the sensor identification information S to U and patient identification information Y that are indicated by the recognized bar codes. The sensor identification information S to U and patient identification information Y that are detected by the identification information detecting section are supplied to the controller 32, and then stored in the storage section 33 as shown in FIG. 9.

Next, the CPU of the receiver 30 reads out, from the storage section 33, the sensor identification information A to C and the patient identification information E, the sensor identification information O to Q and the patient identification information I, and the sensor identification information S to U and the patient identification information Y, produces the first association information associating the sensor identification information A to C and the patient identification information E with each other, that associating the sensor identification information O to Q and the patient identification information I with each other, and that associating the sensor identification information S to U and the patient identification information Y with each other (step S18), and transmits (for example, broadcasts or advertises) the produced first association information (the sensor identification information A to C and the patient identification information E, the sensor identification information O to Q and the patient identification information I, and the sensor identification information S to U and the patient identification information Y) to the physiological information detection sensor 20 through the wireless communicating section 34 (step S20).

When the wireless communicating section 25 receives the first association information (the sensor identification information A to C and the patient identification information E, the sensor identification information O to Q and the patient identification information I, and the sensor identification information S to U and the patient identification information Y), then, the CPU of the physiological information detection sensor 20 causes the received first association information (the sensor identification information A to C and the patient identification information E, the sensor identification information O to Q and the patient identification information I, and the sensor identification information S to U and the patient identification information Y) to be stored in the storage section 24 or the like of the physiological information detection sensor 20. Then, the CPU (the determining section 23a) of the physiological information detection sensor 20 determines whether or not the received first association information (the sensor identification information A to C and the patient identification information E, the sensor identification information O to Q and the patient identification information I, and the sensor identification information S to U and the patient identification information Y) contains the sensor identification information of the own sensor which is previously stored in the storage section 24 (step S22).

If the CPU of the physiological information detection sensor 20 determines that the received first association information (the sensor identification information A to C and the patient identification information E, the sensor identification information O to Q and the patient identification information I, and the sensor identification information S to U and the patient identification information Y) contains the sensor identification information of the own sensor which is previously stored in the storage section 24 (step S22: Yes), the CPU establishes connection with the receiver 30, reads out the sensor identification information of the own sensor, and the patient identification information associated with the sensor identification information of the own sensor from the storage section 24, produces the second association information associating the sensor identification information of the own sensor, the patient identification information, and the physiological information of the patient 50 which is detected by the physiological information detector 21, with one another (step S24), and transmits the produced second association information (the sensor identification information, the patient identification information, and the physiological information of the patient 50) to the receiver 30 through the wireless communicating section 25 (step S26).

Figure 10:
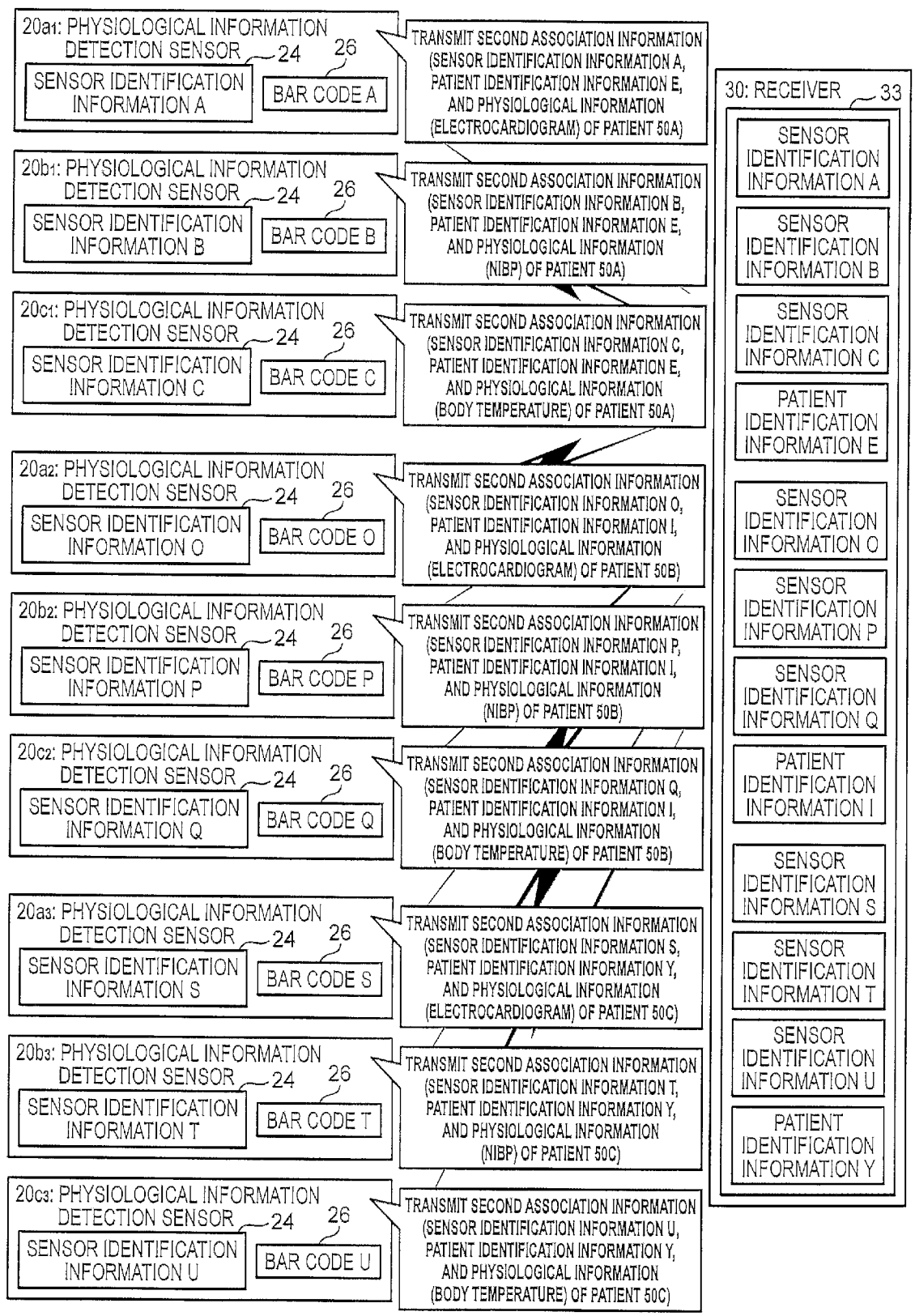
FIG. 10 is a diagram showing a manner in which the physiological information detection sensors 20 transmit second association information (the sensor identification information, the patient identification information, and the physiological information of the patients 50A to 50C).

If the CPU of the physiological information detection sensor $20a_1$ attached to the patient 50A determines that the received first association information (the sensor identification information A to C and the patient identification information E, the sensor identification information O to Q and the patient identification information I, and the sensor identification information S to U and the patient identification information Y) contains the sensor identification information A of the own sensor which is stored in the storage section 24 (step S22: Yes), for example, the CPU establishes connection with the receiver 30, reads out the sensor identification information A of the own sensor, and the patient identification information E associated with the sensor identification information A of the own sensor from the storage section 24, produces the second association information associating the sensor identification information A of the own sensor, the patient identification information E, and the physiological information (electrocardiogram data) of the patient 50A which is detected by the physiological information detector 21, with one another (step S24), and, as shown in FIG. 10, transmits the produced second association information (the sensor identification information A, the patient identification information E, and the physiological information (electrocardiogram data) of the patient 50A) to the receiver 30 through the wireless communicating section 25 (step S26). Similarly, the physiological information detection sensor $20b_1$ (the wireless communicating section 34) attached to the patient 50A transmits the second association information (the sensor identification information B, the patient identification information E, and the physiological information (NIBP data) of the patient 50A) to the receiver 30 (step S26). Similarly, the physiological information detection sensor $20c_1$ (the wireless communicating section 34) attached to the patient 50A transmits the second association information (the sensor identification information C, the patient identification information E, and the physiological information (body temperature data) of the patient 50A) to the receiver 30 (step S26).

If the CPU of the physiological information detection sensor $20a_2$ attached to the patient 50B determines that the received first association information (the sensor identification information A to C and the patient identification information E, the sensor identification information O to Q and the patient identification information I, and the sensor identification information S to U and the patient identification information Y) contains the sensor identification information O of the own sensor which is stored in the storage section 24 (step S22: Yes), for example, the CPU establishes connection with the receiver 30, reads out the sensor identification information O of the own sensor, and the patient identification information I associated with the sensor identification information O of the own sensor from the storage section 24, produces the second association information associating the sensor identification information O of the own sensor, the patient identification information I, and the physiological information (electrocardiogram data) of the patient 50B which is detected by the physiological information detector 21, with one another (step S24), and, as shown in FIG. 10, transmits the produced second association information (the sensor identification information O, the patient identification information I, and the physiological information (electrocardiogram data) of the patient 50B) to the receiver 30 through the wireless communicating section 25 (step S26). Similarly, the physiological information detection sensor $20b_2$ (the wireless communicating section 34) attached to the patient 50B transmits the second association information (the sensor identification information P, the patient identification information I, and the physiological information (NIBP data) of the patient 50B) to the receiver 30 (step S26). Similarly, the physiological information detection sensor $20c_2$ (the wireless communicating section 34) attached to the patient 50B transmits the second association information (the sensor identification information Q, the patient identification information I, and the physiological information (body temperature data) of the patient 50B) to the receiver 30 (step S26).

If the CPU of the physiological information detection sensor $20a_3$ attached to the patient 50C determines that the received first association information (the sensor identification information A to C and the patient identification information E, the sensor identification information O to Q and the patient identification information I, and the sensor identification information S to U and the patient identification information Y) contains the sensor identification information S of the own sensor which is stored in the storage section 24 (step S22: Yes), for example, the CPU establishes connection with the receiver 30, reads out the sensor identification information S of the own sensor, and the patient identification information Y associated with the sensor identification information S of the own sensor from the storage section 24, produces the second association information associating the sensor identification information S of the own sensor, the patient identification information Y, and the physiological information (electrocardiogram data) of the patient 50C which is detected by the physiological information detector 21, with one another (step S24), and, as shown in FIG. 10, transmits the produced second association information (the sensor identification information S, the patient identification information Y, and the physiological information (electrocardiogram data) of the patient 50B) to the receiver 30 through the wireless communicating section 25 (step S26). Similarly, the physiological information detection sensor $20b_3$ (the wireless communicating section 34) attached to the patient 50C transmits the second association information (the sensor identification information T, the patient identification information Y, and the physiological information (NIBP data) of the patient 50C) to the receiver 30 (step S26). Similarly, the physiological information detection sensor $20c_3$ (the wireless communicating section 34) attached to the patient 50C transmits the second association information (the sensor identification information U, the patient identification information Y, and the physiological information (body temperature data) of the patient 50C) to the receiver 30 (step S26).

When the wireless communicating section 34 receives the second association information transmitted by the physiological information detection sensor 20, then, the receiver 30 transmits (transfers) the received second identification information to the physiological information display device 40 (step S28).

When the physiological information display device 40 receives the second association information transmitted by the receiver 30 (or the physiological information detection sensor 20), then, the device displays the received second association information (the sensor identification information, the patient identification information, and the physiological information of the patient 50) on the display provided in the physiological information display device 40 (step S30).

Figure 11:
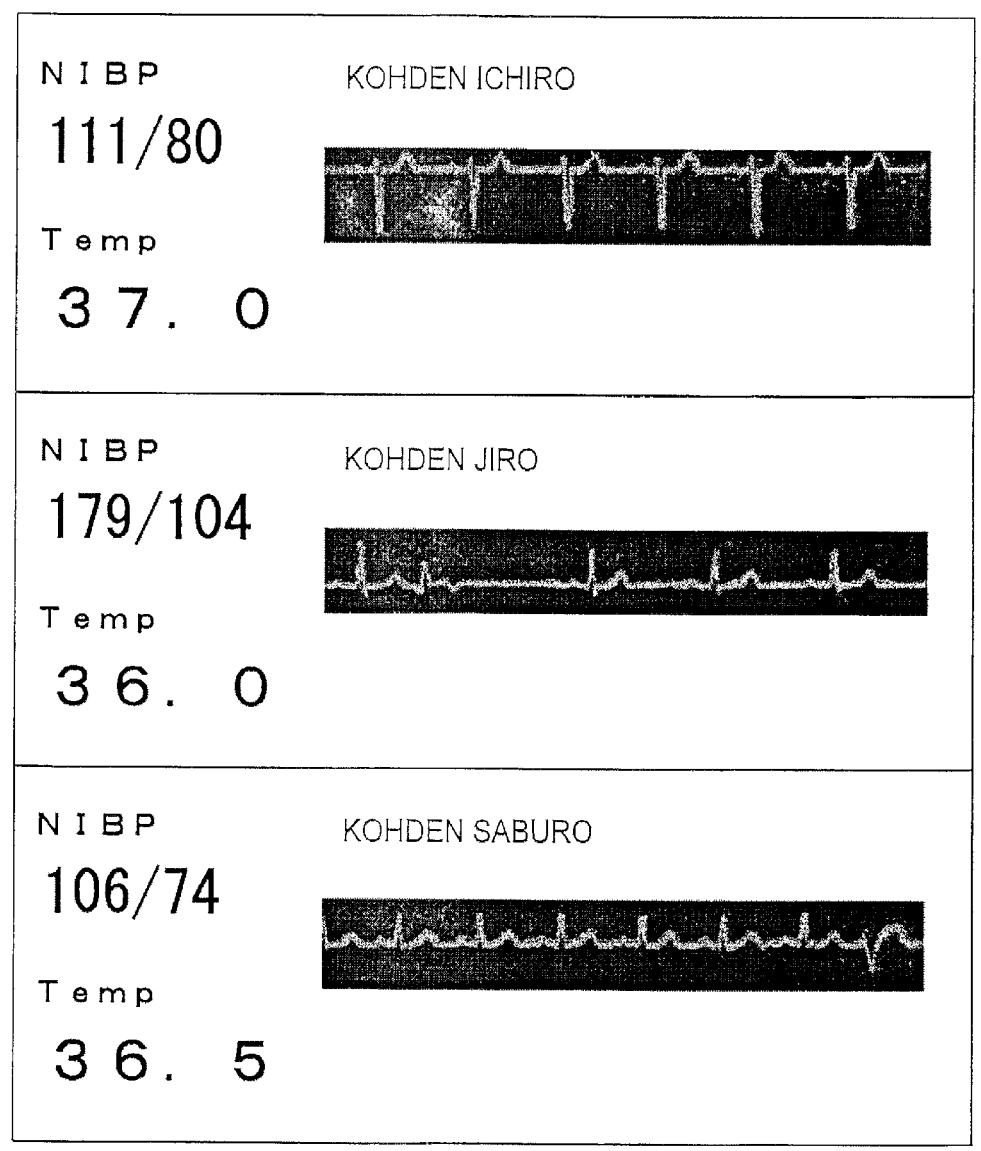
FIG. 11 is a view showing a display example of the second association information (the sensor identification information, the patient identification information, and the physiological information of the patients 50A to 50C).

As shown in FIG. 11, for example, the patient name, the electrocardiogram, the NIBP, and the TEMP are displayed in a predetermined region of the display provided in the physiological information display device 40. FIG. 11 shows a display example of the second association information (the sensor identification information, the patient identification information, and the physiological information of the patient 50). For example, the patient name can be acquired by referring correspondence relationships between the patient identification information E and the patient name, and held by an electronic medical chart (not shown).

According to the operation example, as described above, it is possible to provide a physiological information transmission system, physiological information detection sensor, information processing apparatus, and physiological information transmission method in which the person from whom the physiological information that is wirelessly transmitted by the physiological information detection sensor 20 originates can be easily known.

This is because, first, the receiver 30 acquires the sensor identification information A to C, O to Q, S to U of the physiological information detection sensors 20 attached to the patients 50A to 50C, and the patient identification information E, I, Y of the patients 50A to 50C, and transmits the first association information associating the sensor identification information A to C and patient identification information E which are acquired, with each other, that associating the sensor identification information O to Q and patient identification information I which are acquired, with each other, and that associating the sensor identification information S to U and patient identification information Y which are acquired, with each other. Secondly, the physiological information detection sensor 20 receives the first association information (the sensor identification information A to C and the patient identification information E, the sensor identification information O to Q and the patient identification information I, and the sensor identification information S to U and the patient identification information Y) which is transmitted by the receiver 30, and determines whether or not the received first association information (the sensor identification information A to C and the patient identification information E, the sensor identification information O to Q and the patient identification information I, and the sensor identification information S to U and the patient identification information Y) contains the sensor identification information of the own sensor. If the received first association information (the sensor identification information A to C and the patient identification information E, the sensor identification information O to Q and patient identification information I, and the sensor identification information S to U and patient identification information Y) contains the sensor identification information of the own sensor, the physiological information detection sensor transmits, to the outside of the own sensor, the second association information associating the patient identification information associated with the sensor identification information of the own sensor in the received first association information (the sensor identification information A to C and the patient identification information E, the sensor identification information O to Q and the patient identification information I, and the sensor identification information S to U and the patient identification information Y), the sensor identification information of the own sensor, and the physiological information which is detected by the physiological information detection sensor 20, with one another.

That is, the physiological information detection sensor 20 transmits the physiological information of the patients 50A to 50C which are detected by the physiological information detection sensor 20, as the second association information associated with the sensor identification information of the own sensor and the patient identification information, and therefore the party (for example, the receiver 30) that receives the second association information can easily know the persons from whom the received physiological information of the patients 50A to 50C 50 originate.

Operation Example in Case Where Nurse Identification Information is Used

Figure 12:
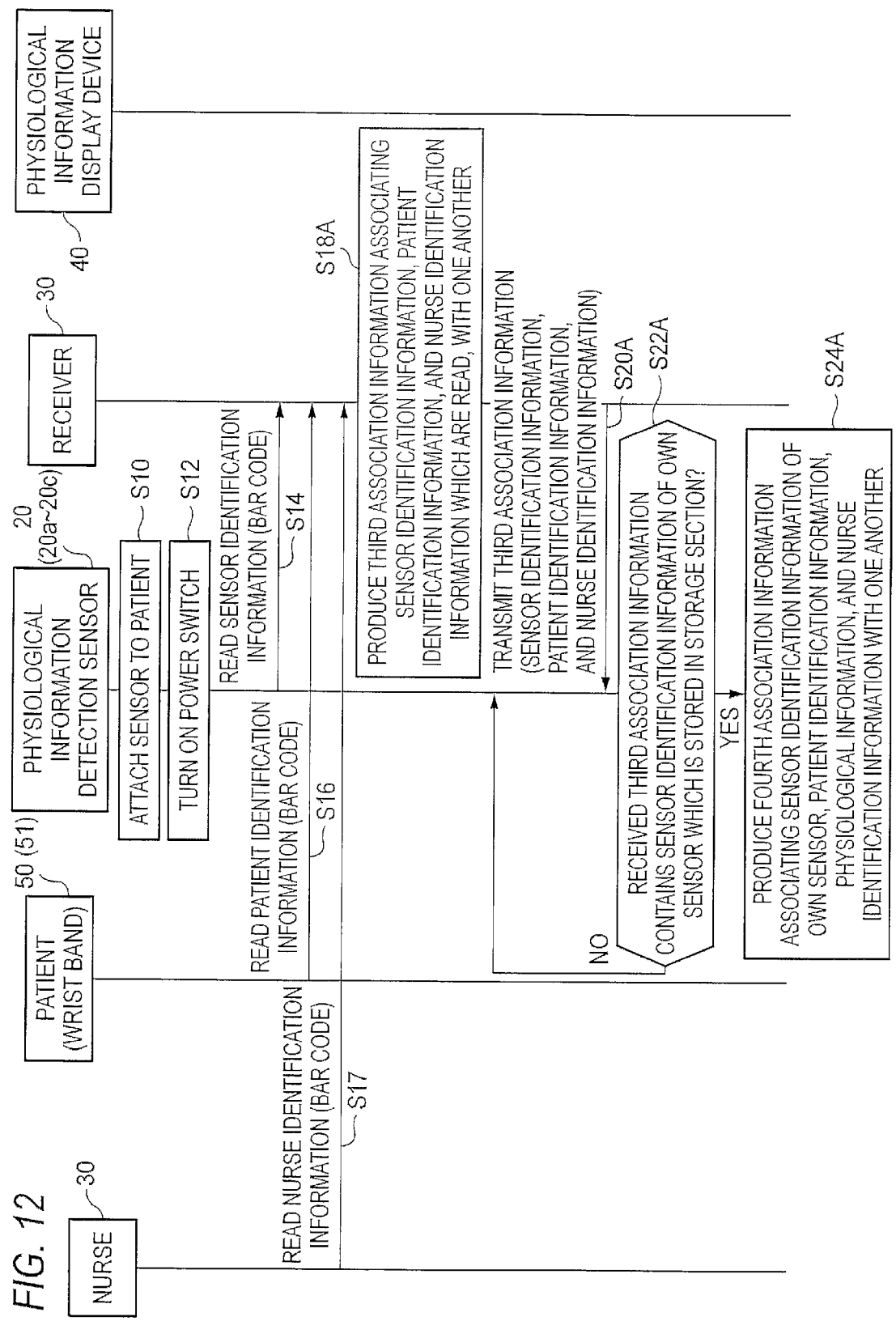
FIG. 12 is a sequence diagram illustrating another operation of the medical telemeter system 10.
Figure 13:
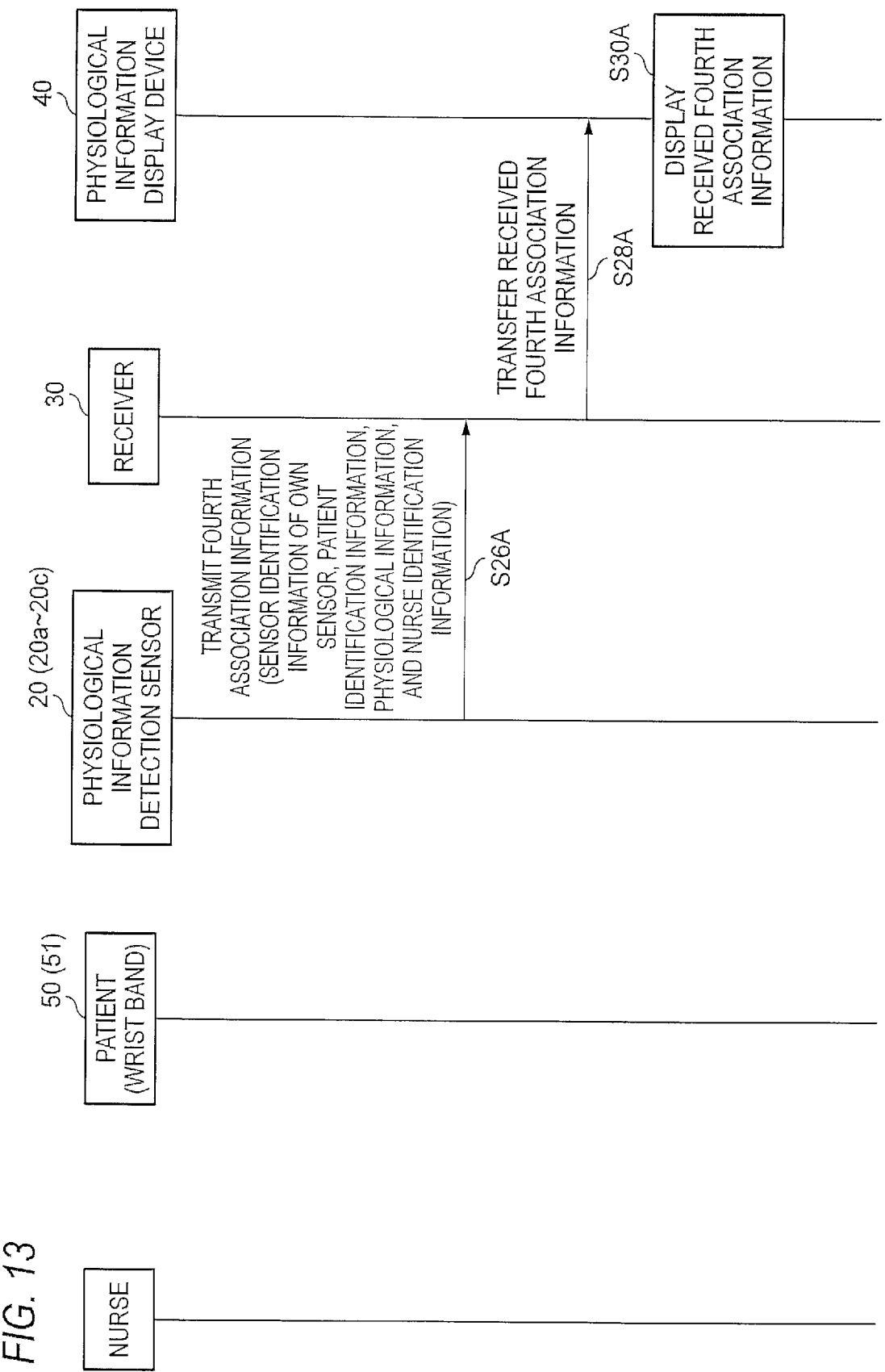
FIG. 13 is a sequence diagram illustrating the other operation of the medical telemeter system 10.

Next, another operation example of the thus configured medical telemeter system 10 will be described. FIGS. 12 and 13 are sequence diagrams illustrating another operation of the medical telemeter system 10.

The sequence diagrams shown in FIGS. 12 and 13 correspond to diagrams in which a step S17 is mainly added to the sequence diagrams shown in FIGS. 3 and 4. Hereinafter, the processes which are similar to those of the sequence diagrams shown in FIGS. 3 and 4 are denoted by the same reference numerals, and their description is appropriately omitted.

As shown in FIG. 12, first, the physiological information detection sensors 20a to 20c are attached to the patient 50 (step S10), and the power switches (not shown) of the respective physiological information detection sensors 20a to 20c are turned ON (step S12). This causes the wireless communicating sections 25 of the respective physiological information detection sensors 20a to 20c to enter a state of waiting for wireless communication from the receiver 30.

Figure 14:
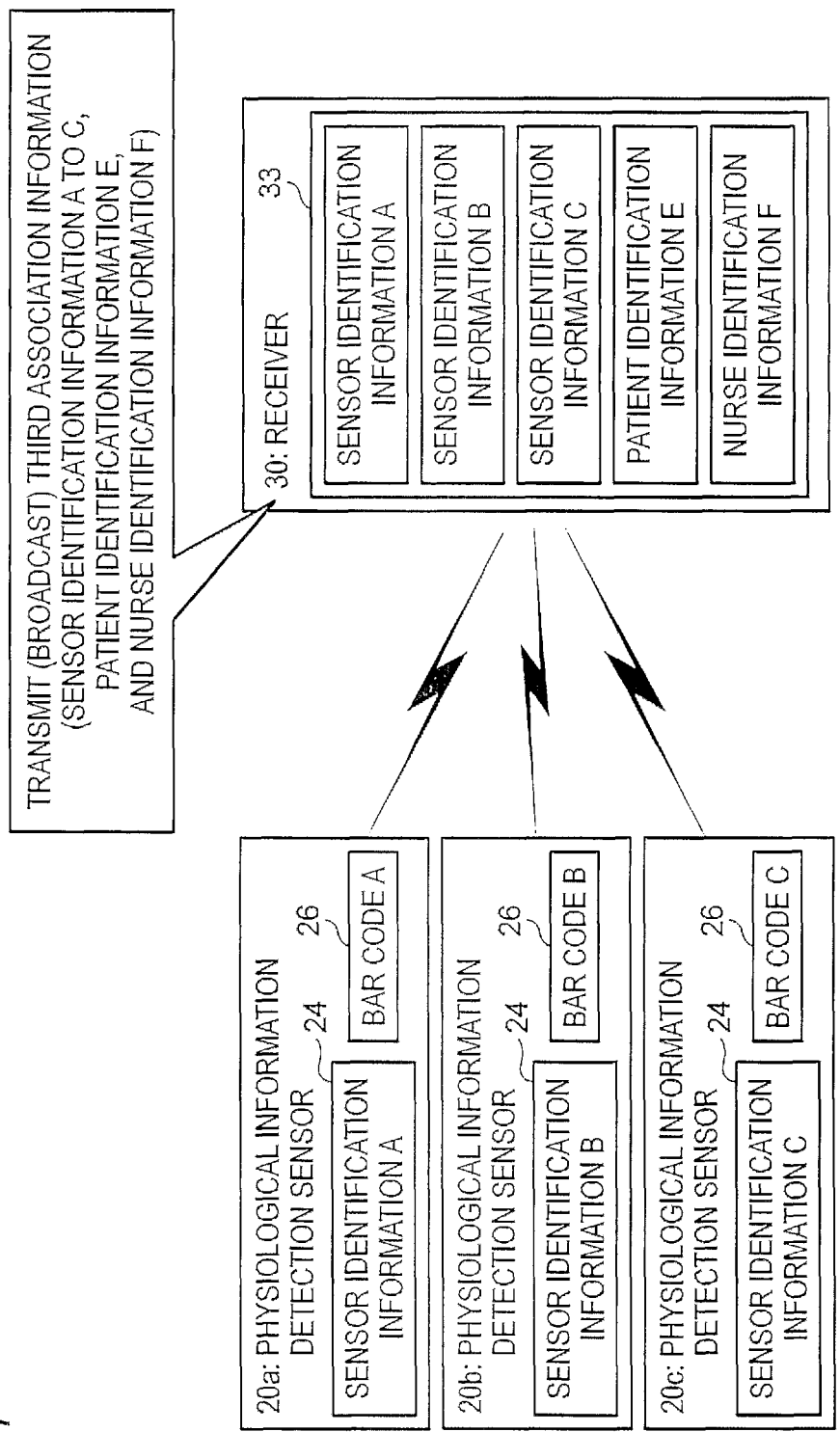
FIG. 14 is a diagram showing a manner in which the receiver 30 transmits (broadcasts) third association information (the sensor identification information A to C, the patient identification information E, and nurse identification information F) to the physiological information detection sensors 20.

Next, the bar codes A to C which are recorded on the respective sensor identification information storage sections 26 of the physiological information detection sensors 20a to 20c attached to the patient 50 are read (step S14). Then, the bar code E which is recorded on the wristband 51 attached to the patient 50 is read (step S16), and thereafter a bar code F which is recorded on a name tag or the like that is attached to the nurse (or another medical person) who has performed these reading works (step S17). Specifically, images of the bar codes A to C which are recorded on the respective sensor identification information storage sections 26 of the physiological information detection sensors 20a to 20c, the bar code E which is recorded on the wristband 51 attached to the patient 50, and the bar code F which is recorded on the name tag or the like which is attached to the nurse (or another medical person) are sequentially taken by the camera such as a CCD camera disposed in the receiver 30. The bar code recognizing section recognizes the bar codes A to C, E, F based on the taken images. Then, the identification information detecting section detects the sensor identification information A to C, patient identification information E, and nurse identification information F that are indicated by the recognized bar codes. The sensor identification information A to C, patient identification information E, and nurse identification information F that are detected by the identification information detecting section are supplied to the controller 32, and then stored in the storage section 33 as shown in FIG. 14. FIG. 14 is a diagram showing a manner in which the receiver 30 transmits (broadcasts) third association information (the sensor identification information A to C, the patient identification information E, and the nurse identification information F) to the physiological information detection sensors 20.

Next, the CPU of the receiver 30 reads out the sensor identification information A to C, the patient identification information E, and the nurse identification information F from the storage section 33, produces the third association information associating the sensor identification information A to C, the patient identification information E, and the nurse identification information F with one another (step S18A), and, as shown in FIG. 14, transmits (for example, broadcasts or advertises) the third association information (the sensor identification information A to C, the patient identification information E, and the nurse identification information F) to the physiological information detection sensor 20 through the wireless communicating section 34 (step S20A).

When the wireless communicating section 25 receives the third association information (the sensor identification information A to C, the patient identification information E, and the nurse identification information F), then, the CPU of the physiological information detection sensor 20 causes the received third association information (the sensor identification information A to C, the patient identification information E, and the nurse identification information F) to be stored in the storage section 24 or the like of the physiological information detection sensor 20. Then, the CPU (the determining section 23a) of the physiological information detection sensor 20 determines whether the received third association information (the sensor identification information A to C, the patient identification information E, and the nurse identification information F) contains the sensor identification information of the own sensor which is previously stored in the storage section 24 or not (step S22A).

If the CPU of the physiological information detection sensor 20 determines that the received third association information (the sensor identification information A to C, the patient identification information E, and the nurse identification information F) contains the sensor identification information of the own sensor which is previously stored in the storage section 24 (step S22A: Yes), the CPU establishes connection with the receiver 30, reads out the sensor identification information of the own sensor, the patient identification information associated with the sensor identification information of the own sensor, and the nurse identification information from the storage section 24, produces fourth association information associating the sensor identification information of the own sensor, the patient identification information, the physiological information of the patient 50 which is detected by the physiological information detector 21, and the nurse identification information, with one another (step S24A), and transmits the produced fourth association information (the sensor identification information, the patient identification information, the physiological information of the patient 50, and the nurse identification information) to the receiver 30 through the wireless communicating section 25 (step S26A).

Figure 15:
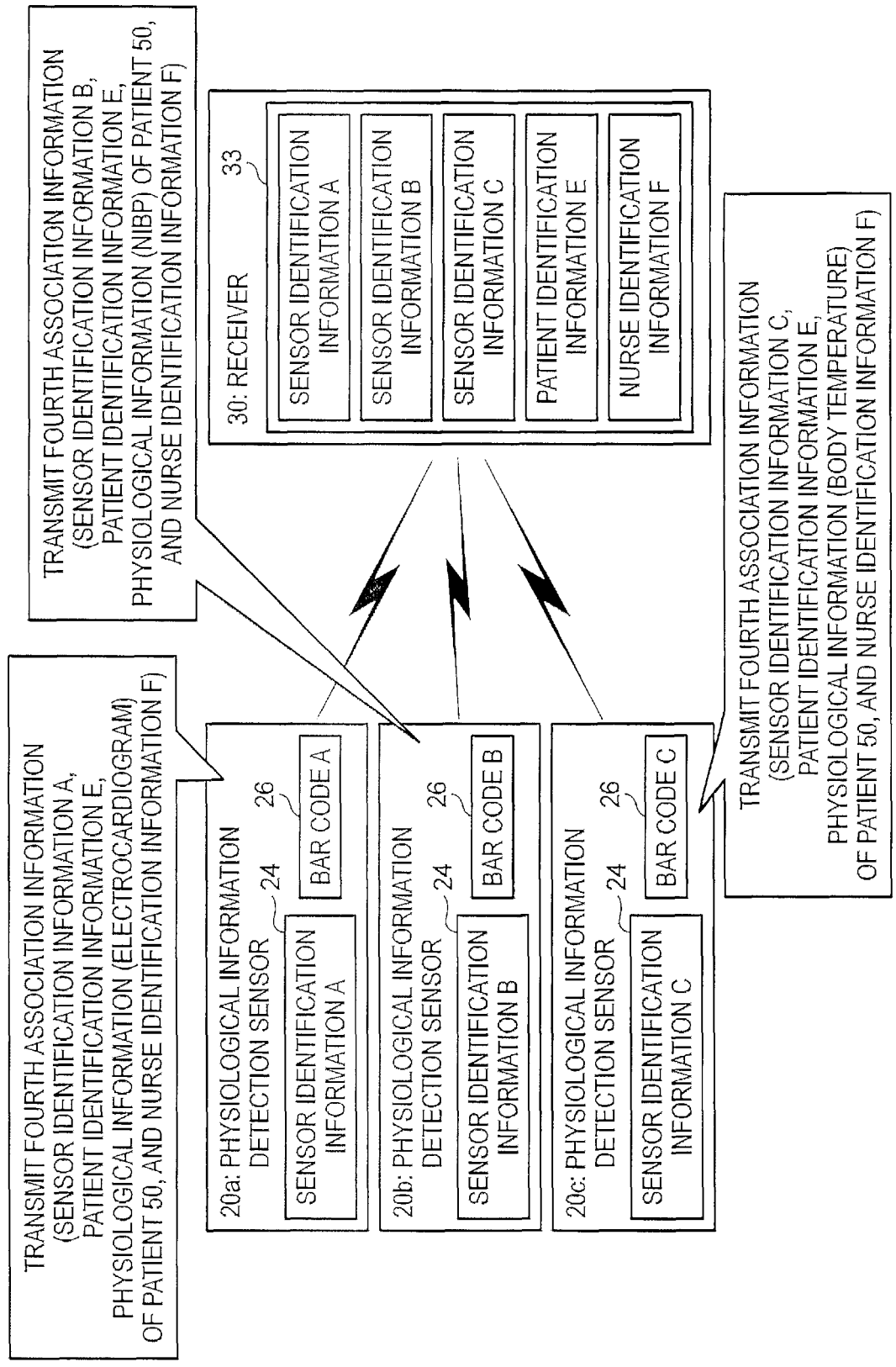
FIG. 15 is a diagram showing a manner in which the physiological information detection sensors 20 transmit fourth association information (the sensor identification information, the patient identification information, the physiological information of the patient 50, and the nurse identification information).

If the CPU of the physiological information detection sensor 20a determines that the received third association information (the sensor identification information A to C, the patient identification information E, and the nurse identification information F) contains the sensor identification information A of the own sensor which is stored in the storage section 24 (step S22A: Yes), for example, the CPU establishes connection with the receiver 30, reads out the sensor identification information A of the own sensor, the patient identification information E associated with the sensor identification information of the own sensor, and the nurse identification information F from the storage section 24, produces the fourth association information associating the sensor identification information A of the own sensor, the patient identification information E, the physiological information (electrocardiogram data) of the patient 50 which is detected by the physiological information detector 21, and the nurse identification information F with one another (step S24A), and, as shown in FIG. 15, transmits the produced fourth association information (the sensor identification information A, the patient identification information E, the physiological information of the patient 50, and the nurse identification information F) to the receiver 30 through the wireless communicating section 25 (step S26A).

If the CPU of the physiological information detection sensor 20b determines that the received third association information (the sensor identification information A to C, the patient identification information E, and the nurse identification information F) contains the sensor identification information B of the own sensor which is stored in the storage section 24 (step S22A: Yes), similarly, the CPU establishes connection with the receiver 30, reads out the sensor identification information B of the own sensor, the patient identification information E associated with the sensor identification information of the own sensor, and the nurse identification information F from the storage section 24, produces the fourth association information associating the sensor identification information B of the own sensor, the patient identification information E, the physiological information (NIBP data) of the patient 50 which is detected by the physiological information detector 21, and the nurse identification information F, with one another (step S24A), and, as shown in FIG. 15, transmits the produced fourth association information (the sensor identification information B, the patient identification information E, the physiological information of the patient 50, and the nurse identification information F) to the receiver 30 through the wireless communicating section 25 (step S26A).

If the CPU of the physiological information detection sensor 20c determines that the received third association information (the sensor identification information A to C, the patient identification information E, and the nurse identification information F) contains the sensor identification information C of the own sensor which is stored in the storage section 24 (step S22A: Yes), similarly, the CPU establishes connection with the receiver 30, reads out the sensor identification information C of the own sensor, the patient identification information E associated with the sensor identification information of the own sensor, and the nurse identification information F, produces the fourth association information associating the sensor identification information C of the own sensor, the patient identification information E, the physiological information (body temperature data) of the patient 50 which is detected by the physiological information detector 21, and the nurse identification information F, with one another (step S24A), and, as shown in FIG. 15, transmits the produced fourth association information (the sensor identification information C, the patient identification information E, the physiological information of the patient 50, and the nurse identification information F) to the receiver 30 (or the physiological information display device 40) through the wireless communicating section 25 (step S26A).

When the wireless communicating section 34 receives the fourth association information transmitted by the physiological information detection sensor 20, then, the receiver 30 transmits (transfers) the received fourth identification information to the physiological information display device 40 (step S28A).

When the physiological information display device 40 receives the fourth association information transmitted by the receiver 30 (or the physiological information detection sensor 20), then, the device displays the received fourth association information (the sensor identification information, the patient identification information, the physiological information of the patient 50, and the nurse identification information) on the display provided in the physiological information display device 40 (step S30A).

As shown in FIG. 7, for example, the patient name, the electrocardiogram, the NIBP, and the TEMP are displayed in the predetermined region of the display provided in the physiological information display device 40. For example, the patient name can be acquired by referring correspondence relationships between the patient identification information E and the patient name, and held by the electronic medical chart (not shown).

The physiological information display device 40 further causes the received fourth association information (the sensor identification information, the patient identification information, the physiological information of the patient 50, and the nurse identification information) to be stored as a history in the storage section provided in the physiological information display device 40.

According to the operation example, as described above, it is possible to easily know who performed reading of the sensor identification information and the patient identification information (so called, the three-point recognition). This is because the physiological information detection sensor 20 transmits, as the fourth association information, the nurse identification information F in addition to the sensor identification information and the patient identification information, and the received fourth association information (the sensor identification information, the patient identification information, the physiological information of the patient 50, and the nurse identification information) is stored as a history in the storage section provided in the physiological information display device 40 or the like, Next, modifications will be described.

In the above, the embodiment in which the physiological information detection sensor 20a that detects an electrocardiogram, the physiological information detection sensor 20b that detects the NIBP, and the physiological information detection sensor 20c that detects the body temperature (TEMP) are used as the physiological information detection sensor 20 has been described. However, the physiological information detection sensor is not limited to them. Other physiological information detection sensors such as a physiological information detection sensor that detects the SpO2 (arterial oxygen saturation) may be used.

In the above, the embodiment in which a display surface of a seal that is pasted to the case 27, an electronic paper sheet, or the like is used as the sensor identification information recording section 26, and the sensor identification information (bar code) identical with that of the own sensor that is stored in the storage section 24 is printed or displayed on the display surface of the seal or the electronic paper sheet has been described. However, the sensor identification information storage section is not limited to this. For example, an RF tag that is pasted to or incorporated in the case 27 may be used as the sensor identification information recording section 26, and sensor identification information identical with that of the own sensor that is stored in the storage section 24 may be stored in the RF tag (correctly, a memory in the RF tag). In this case, for example, a smartphone with reader/writer functions which can wirelessly read out the sensor identification information from the RF tag may be used as the receiver 30. An RF tag is often called also an electronic tag, an IC tag, a wireless tag, or an RF ID tag.

In the above, the embodiment in which communication modules (e.g., BLE modules) compatible to BLE (Bluetooth Low Energy) technology are used as the wireless communicating sections 25, 34 has been described. However, the wireless communicating sections are not limited to this. For example, communication modules (e.g., wireless LAN modules) compatible to wireless LAN technology may be used as the wireless communicating sections 25, 34.

In the above, the embodiment in which association information associating the sensor identification information of the own sensor, the patient identification information, and the physiological information (e.g., electrocardiogram data) of the patient 50 which is detected by the physiological information detector 21, with one another is used as the second association information has been described. However, the second association information is not limited to this. For example, association information in which the sensor identification information of the own sensor is omitted, and the patient identification information and the physiological information (e.g., electrocardiogram data) of the patient 50 that is detected by the physiological information detector 21 are associated with each other may be used as the second association information. Also in this configuration, the party (for example, the receiver 30) which receives the second association information can easily know the person from whom the received physiological information of the patient 50 originates.

In the above, the embodiment in which the means (for example, a camera such as a CCD camera) for optically reading the bar codes A to C and the like is used as the identification information inputting section 31 has been described. However, the identification information inputting section is not limited to this. For example, another inputting section such as a key pad through which a nurse or the like manually inputs the sensor identification information and the patient identification information may be used as the identification information inputting section 31.

Alternatively, for example, the transmission of the first association information in step S20 (see FIG. 3) may be executed by reading the bar codes A to C which are recorded on the respective sensor identification information storage sections 26 of the physiological information detection sensors 20a to 20c attached to the last patient 50, reading the bar code E recorded on the wrist band 51 attached to the last patient 50, and thereafter executing a predetermined operation on the receiver 30. Although not illustrated, for example, the predetermined operation is an operation to be performed on a transmission button which is disposed in the receiver 30 (or a transmission button which is displayed on the display provided in the receiver 30). Similarly, for example, the transmission of the third association information in step S20A (see FIG. 12) may be executed by reading the bar codes A to C which are recorded on the respective sensor identification information storage sections 26 of the physiological information detection sensors 20a to 20c attached to the last patient 50, reading the bar code E recorded on the wrist band 51 attached to the last patient 50, reading the bar code F which is recorded on the name tag or the like that is attached to the nurse (or another medical person) who has performed these reading works, and thereafter executing a predetermined operation on the receiver 30.

All the numerical values indicated in the embodiment are exemplarily shown. It is a matter of course that appropriate numerical values different from the values may be used.

The embodiment is a mere simple example in all aspects. The invention should not be limitedly interpreted by the description of the embodiment. The invention can be implemented in various other ways without departing from the spirit and principal features thereof.

The present application is based on Japanese Patent Application No. 2017-091117 filed on May 1, 2017, the contents of which are incorporated herein by way of reference.

INDUSTRIAL APPLICABILITY

According to the invention, there is provided a physiological information transmission system, physiological information detection sensor, information processing apparatus, and physiological information transmission method in which it is possible to easily know the person from whom physiological information that is wirelessly transmitted by a physiological information detection sensor originates.

The invention claimed is:

1. A physiological information transmission system comprising at least one physiological information detection sensor and a smartphone, wherein the smartphone includes:

a sensor identification information acquiring section configured to acquire sensor identification information of the physiological information detection sensor, the sensor identification information acquiring section being capable of reading a bar code corresponding to the sensor identification information;
a living body identification information acquiring section configured to acquire living body identification information of a living body, the living body identification information being capable of reading a bar code corresponding to the living body identification information;
a controller configured to generate first association information associating the sensor identification information which is acquired by the sensor identification information acquiring section, and the living body identification information of the living body which is acquired by the living body identification information acquiring section with each other; and
a first transmitter configured to transmit the first association information to the physiological information detection sensor through short-range wireless communication, and
the physiological information detection sensor includes:
a physiological information detector configured to detect physiological information of the living body;
at least one storage section configured to store the sensor identification information of the own sensor;
a receiver configured to receive the first association information which is transmitted by the first transmitter of the smartphone through short-range wireless communication;
a determining section configured to determine whether or not the first association information received by the receiver contains the sensor identification information of the own sensor which is stored in the storage section when the receiver receives the first association information; and
a second transmitter which is configured to transmit second association information associating the living body identification information in the received first association information through short-range wireless communication, and the physiological information of the living body which is detected by the physiological information detector, with each other, to an outside of the own sensor in response to a determination that the first association information received by the receiver contains the sensor identification information of the own sensor which is stored in the storage section.

2. The physiological information transmission system according to claim 1, wherein the second association information is association information associating the living body identification information in the received first association information, the sensor identification information of the own sensor, and the physiological information of the living body which is detected by the physiological information detector, with one another.

3. The physiological information transmission system according to claim 1, wherein
the physiological information detection sensor further includes a sensor identification information recording section in which sensor identification information that is identical with the sensor identification information of the own sensor which is stored in the storage section is recorded, and
the sensor identification information acquiring section is configured to acquire the sensor identification information of the physiological information detection sensor from the sensor identification information recording section.

4. The physiological information transmission system according to claim 1, wherein the outside of the own sensor is a display device configured to display the second association information which is transmitted by the second transmitter, or a transfer device which is configured to transfer the second association information which is transmitted by the second transmitter, to the display device.

5. The physiological information transmission system according to claim 1, wherein
the smartphone further includes a medical person identification information acquiring section configured to acquire identification information of a medical person who acquires the sensor identification information and the living body identification information,
the first association information is association information associating: the sensor identification information which is acquired by the sensor identification information acquiring section; the living body identification information of the living body which is acquired by the living body identification information acquiring section; and the medical person identification information which is acquired by the medical person identification information acquiring section, with one another, and
the second association information is association information associating: the living body identification information and medical person identification information in the received first association information; and the physiological information of the living body which is detected by the physiological information detector, with each other.

6. A physiological information detection sensor comprising:
a physiological information detector configured to detect physiological information of a living body;
at least one storage section configured to store sensor identification information of the own sensor, the sensor identification information being read from a bar code;
a receiver configured to receive first association information generated and transmitted by a smartphone through short-range wireless communication, the first association information associating the sensor identification information and living body identification information of the living body with each other, the living body identification information being read from a bar code;
a determining section configured to determine whether or not the first association information received by the receiver contains the sensor identification information of the own sensor which is stored in the storage section when the receiver receives the first association information; and
a transmitter which is configured to establish a connection between the physiological information detection sensor and the smartphone and to transmit second association information associating the living body identification information in the received first association information through short-range wireless communication, and the physiological information of the living body which is detected by the physiological information detector, with each other, to an outside of the own sensor in response to a determination that the first association information received by the receiver contains the sensor identification information of the own sensor which is stored in the storage section.

7. The physiological information detection sensor according to claim 6, further comprising a sensor identification information recording section in which sensor identification information that is identical with the sensor identification information of the own sensor which is stored in the storage section is recorded.

8. A smartphone comprising:
- a sensor identification information acquiring section configured to acquire sensor identification information of a physiological information detection sensor which is adapted to be attached to a living body, wherein the sensor identification information acquiring section being capable of reading a bar code corresponding to the sensor identification information;
- a living body identification information acquiring section configured to acquire living body identification information of the living body, wherein the living body identification information acquiring section being capable of reading a bar code corresponding to the sensor identification information;
- a controller configured to generate first association information associating the sensor identification information which is acquired by the sensor identification information acquiring section, and the living body identification information of the living body which is acquired by the living body identification information acquiring section, with each other; and
- a first transmitter configured to transmit the first association information to the physiological information detection sensor through short-range wireless communication,
- wherein the smartphone makes the physiological information detection sensor determine whether or not the first association information received by the receiver contains the sensor identification information of the own sensor which is stored in the storage section when the receiver receives the first association information, and
- wherein the smartphone transmits second association information associating the living body identification information in the received first association information through short-range wireless communication, and the physiological information of the living body which is detected by the physiological information detector, with each other, to an outside of the own sensor in response to a determination that the first association information received by the receiver contains the sensor identification information of the own sensor which is stored in the storage section.

9. A physiological information transmission method comprising:
- by a smartphone:
- acquiring sensor identification information of a physiological information detection sensor which is adapted to be attached to a living body, and living body identification information of the living body, the sensor identification information being read from a bar code, and the living body identification information being read from a bar code;
- generating first association information associating the sensor identification information and the living body identification information of the living body with each other, and transmitting first association information to the physiological information detection sensor through short-range wireless communication; and
- by the physiological information detection sensor:
- receiving the first association information;
- determining whether or not the received first association information contains sensor identification information of the own sensor when the first association information is received; and
- transmitting second association information associating the living body identification information in the received first association information through short-range wireless communication, and physiological information which is detected by the physiological information detection sensor, with each other, to an outside of the own sensor in response to a determination that the first association information contains the sensor identification information of the own sensor.

10. The physiological information transmission system according to claim 1, wherein the short-range wireless communication is communication within 100 mm.

* * * * *